(12) United States Patent
Fogarty

(10) Patent No.: US 8,241,203 B2
(45) Date of Patent: Aug. 14, 2012

(54) INFLATABLE PENILE PROSTHESIS WITH SPOOL VALVE

(76) Inventor: Terence M. Fogarty, Hudson, WI (US)

( * ) Notice: Subject to any disclaimer, the term of this patent is extended or adjusted under 35 U.S.C. 154(b) by 19 days.

(21) Appl. No.: 13/025,364

(22) Filed: Feb. 11, 2011

(65) Prior Publication Data
US 2011/0201880 A1 Aug. 18, 2011

Related U.S. Application Data

(60) Provisional application No. 61/304,171, filed on Feb. 12, 2010, provisional application No. 61/359,687, filed on Jun. 29, 2010.

(51) Int. Cl.
*A61F 5/00* (2006.01)
(52) U.S. Cl. ........................................................ 600/40
(58) Field of Classification Search ............... 600/38–41
See application file for complete search history.

(56) References Cited

U.S. PATENT DOCUMENTS

| | | | |
|---|---|---|---|
| 3,853,122 A | 12/1974 | Strauch et al. |
| 3,954,102 A | 5/1976 | Buuck |
| 4,201,202 A | 5/1980 | Finney et al. |
| 4,235,227 A | 11/1980 | Yamanaka |
| 4,267,829 A | 5/1981 | Burton et al. |
| 4,318,396 A | 3/1982 | Finney |
| 4,342,308 A | 8/1982 | Trick |
| 4,353,360 A | 10/1982 | Finney et al. |
| 4,360,010 A | 11/1982 | Finney |
| 4,364,379 A | 12/1982 | Finney |
| 4,369,771 A | 1/1983 | Trick |
| 4,378,792 A | 4/1983 | Finney |
| 4,383,525 A | 5/1983 | Scott et al. |
| 4,399,811 A | 8/1983 | Finney et al. |
| 4,399,812 A | 8/1983 | Whitehead |
| 4,404,968 A | 9/1983 | Evans |
| 4,407,278 A | 10/1983 | Burton et al. |
| 4,411,261 A | 10/1983 | Finney |
| 4,424,807 A | 1/1984 | Evans |
| 4,441,491 A | 4/1984 | Evans |
| 4,449,520 A | 5/1984 | Palomar et al. |
| 4,550,719 A | 11/1985 | Finney et al. |
| 4,550,720 A | 11/1985 | Trick |
| 4,558,693 A | 12/1985 | Lash et al. |
| 4,559,931 A | 12/1985 | Fischell |
| 4,566,446 A | 1/1986 | Fogarty |
| 4,572,168 A | 2/1986 | Fischell |
| 4,574,792 A | 3/1986 | Trick |
| 4,584,994 A | 4/1986 | Bamberger et al. |
| 4,590,927 A | 5/1986 | Porter et al. |
| 4,594,997 A | 6/1986 | Hakky |
| 4,596,242 A | 6/1986 | Fischell |
| 4,597,765 A | 7/1986 | Klatt |
| 4,602,621 A | 7/1986 | Hakky |
| 4,602,625 A | 7/1986 | Yachia et al. |
| 4,622,958 A | 11/1986 | Finney |
| 4,651,721 A | 3/1987 | Mikulich et al. |
| 4,665,903 A | 5/1987 | Whitehead |
| 4,671,261 A | 6/1987 | Fischell |

(Continued)

*Primary Examiner* — John Lacyk
(74) *Attorney, Agent, or Firm* — Allen J. Oh Law Office

(57) ABSTRACT

According to various embodiments, an inflatable penile prosthesis (IPP) includes a rigidly constructed spool valve assembly that is used to direct fluid into and evacuate fluid out of the inflatable penile cylinders. The fluid transfer system transfers fluid from the fluid reservoir to the inflatable penile cylinders and includes the fluid transfer bulb, inlet valve, exhaust valve and spool valve assembly. The cylinder deflate mechanism evacuates fluid from the penile cylinders to the reservoir and includes the deflate actuator, return valve and spool valve assembly.

25 Claims, 18 Drawing Sheets

U.S. PATENT DOCUMENTS

| | | | |
|---|---|---|---|
| 4,682,589 | A | 7/1987 | Finney |
| 4,711,231 | A | 12/1987 | Finegold et al. |
| 4,718,410 | A | 1/1988 | Hakky |
| 4,726,360 | A | 2/1988 | Trick et al. |
| 4,742,830 | A | 5/1988 | Tamano et al. |
| 4,773,403 | A | 9/1988 | Daly |
| 4,782,826 | A | 11/1988 | Fogarty |
| 4,791,917 | A | 12/1988 | Finney |
| 4,823,779 | A | 4/1989 | Daly et al. |
| 4,852,555 | A | 8/1989 | Trick |
| 4,875,472 | A | 10/1989 | Levius |
| 4,881,530 | A | 11/1989 | Trick |
| 4,895,139 | A | 1/1990 | Hauschild et al. |
| 4,898,158 | A | 2/1990 | Daly et al. |
| 4,917,110 | A | 4/1990 | Trick |
| 4,941,461 | A | 7/1990 | Fischell |
| 4,995,380 | A | 2/1991 | Maerzke et al. |
| 5,010,882 | A | 4/1991 | Polyak et al. |
| 5,048,510 | A | 9/1991 | Hauschild et al. |
| 5,062,416 | A | 11/1991 | Stucks |
| 5,062,417 | A | 11/1991 | Cowen |
| 5,063,914 | A | 11/1991 | Cowen |
| 5,067,485 | A | 11/1991 | Cowen |
| 5,069,201 | A | 12/1991 | Zinner et al. |
| 5,101,813 | A | 4/1992 | Trick |
| 5,112,295 | A | 5/1992 | Zinner et al. |
| 5,141,509 | A | 8/1992 | Burton et al. |
| 5,167,611 | A | 12/1992 | Cowan |
| 5,171,272 | A | 12/1992 | Levius |
| 5,250,020 | A | 10/1993 | Bley |
| 5,263,981 | A | 11/1993 | Polyak et al. |
| 5,344,388 | A | 9/1994 | Maxwell et al. |
| 5,437,605 | A | 8/1995 | Helmy |
| 5,699,870 | A | 12/1997 | Warren |
| 5,704,895 | A | 1/1998 | Scott et al. |
| 5,803,897 | A | 9/1998 | Mooreville et al. |
| 5,851,176 | A | 12/1998 | Willard |
| 5,895,424 | A | 4/1999 | Steele et al. |
| 5,899,849 | A | 5/1999 | Elist |
| 6,171,233 | B1 | 1/2001 | Willard |
| 6,443,887 | B1 | 9/2002 | Derus et al. |
| 6,475,137 | B1 | 11/2002 | Elist |
| 6,533,719 | B2 | 3/2003 | Kuyava et al. |
| 6,558,315 | B1 | 5/2003 | Kuyava |
| 6,703,017 | B1 | 3/2004 | Peck et al. |
| 6,723,042 | B2 | 4/2004 | Almli et al. |
| 6,808,489 | B2 | 10/2004 | George et al. |
| 6,808,490 | B1 | 10/2004 | Ling et al. |
| 6,929,599 | B2 | 8/2005 | Westrum |
| 6,991,601 | B2 | 1/2006 | Kuyava et al. |
| 7,011,624 | B2 | 3/2006 | Forsell |
| 7,066,877 | B2 | 6/2006 | Kuyava |
| 7,169,103 | B2 | 1/2007 | Ling et al. |
| 7,244,227 | B2 | 7/2007 | Morningstar |
| 7,250,026 | B2 | 7/2007 | Kuyava |
| 7,350,538 | B2 | 4/2008 | Kuyava et al. |
| 7,438,682 | B2 | 10/2008 | Henkel et al. |
| 7,491,164 | B2 | 2/2009 | Choi et al. |
| 7,637,861 | B2 | 12/2009 | Kuyava et al. |
| 7,717,845 | B2 | 5/2010 | George et al. |
| 7,874,978 | B2 | 1/2011 | Kuyava et al. |
| 2002/0091302 | A1 | 7/2002 | Kuyava et al. |
| 2003/0065249 | A1 | 4/2003 | Kuyava et al. |
| 2004/0193005 | A1 | 9/2004 | Almli et al. |
| 2004/0215056 | A1 | 10/2004 | Ling et al. |
| 2005/0228220 | A1 | 10/2005 | Westrum |
| 2006/0235267 | A1 | 10/2006 | George et al. |
| 2007/0142700 | A1 | 6/2007 | Fogarty et al. |
| 2008/0114202 | A1 | 5/2008 | Kuyava et al. |
| 2009/0253953 | A1 | 10/2009 | Morningstar |
| 2009/0287042 | A1 | 11/2009 | Almli et al. |
| 2010/0036196 | A1 | 2/2010 | Walch |

INFLATABLE PENILE PROSTHESIS WITH SPOOL VALVE

CROSS REFERENCE TO RELATED APPLICATIONS

This application claims the benefit of priority to provisional application 61/304,171, filed Feb. 12, 2010, and to provisional application 61/359,687, filed Jun. 29, 2010. The disclosures of the aforementioned provisional applications are incorporated herein in their entirety.

TECHNICAL FIELD

This disclosure relates generally to prosthetic medical devices and methods of using such devices in implant surgery. More particularly, this disclosure relates to implantable inflatable penile prostheses used to treat male impotence.

BACKGROUND

Historically, implantable penile prosthesis, both the inflatable type and non-inflatable type that include rigid, mechanical and malleable devices have been supplied with paired penile cylinders. Inflatable penile prostheses (IPP) typically include a pair of inflatable penile cylinders, a fluid transfer pump, a deflate mechanism, a fluid storage reservoir and flexible tubing connecting components. There are three basic categories of inflatable penile prostheses: one-piece, two-piece and three-piece IPP devices. One-piece inflatable penile prostheses are configured with an inflatable bladder, pump, deflate mechanism and reservoir wholly contained in each of the two unitary paired penile cylinders that are implanted in their entirety in the corpora cavernosa of the penis. Two-piece inflatable penile prostheses are configured with paired inflatable penile cylinders implanted in the corpora cavernosa of the penis. At least one of the other components (i.e., the fluid transfer pump, the deflate mechanism, or the fluid reservoir) is implanted outside the corpora cavernosa. Three-piece inflatable penile prostheses are configured with paired inflatable penile cylinders implanted in the corpora cavernosa of the penis. At least two of the other components (i.e., the fluid transfer pump, the deflate mechanism, or the fluid reservoir) are implanted outside the corpora cavernosa.

One-piece and two-piece inflatable penile prostheses have included a fluid storage chamber or reservoir within the cylinder component implanted in the corpus cavernosum, with the reservoir configured distal to the inflatable bladder as disclosed by Burton et al. in U.S. Pat. No. 4,267,829. The reservoir has been configured proximal to the inflatable bladder (e.g., Finney, U.S. Pat. No. 4,318,396), within inflatable bladders (e.g., Whitehead, U.S. Pat. No. 4,665,903), or surrounding the inflatable bladder (e.g., Finney, U.S. Pat. No. 4,353,360). Two-piece inflatable penile prosthesis have also been configured with a reservoir implanted outside the corpora cavernosa and supplying fluid to one or both inflatable penile cylinders (e.g., Uson, U.S. Pat. No. 4,009,711). Three-piece inflatable penile prostheses have been configured with a single reservoir implanted outside the corpora cavernosa and supplying fluid to both penile inflatable cylinders (e.g., Buuck, U.S. Pat. No. 3,954,102). Each of the cited patents is incorporated by reference in its entirety.

SUMMARY

The present disclosure relates to a departure from the design of fluid transfer systems and cylinder deflate mechanisms previously used in two and three-piece inflatable penile prostheses. According to various embodiments, a rigidly constructed spool valve assembly is used to direct fluid into and evacuate fluid out of the inflatable penile cylinders. The fluid transfer system transfers fluid from the fluid reservoir to the inflatable penile cylinders and includes the fluid transfer bulb, inlet valve, exhaust valve and spool valve assembly. The cylinder deflate mechanism evacuates fluid from the penile cylinders to the reservoir and includes the deflate actuator, return valve and spool valve assembly.

The principles disclosed herein can be practiced in connection with, for example, a two-piece or three-piece inflatable penile prosthesis having paired inflatable penile cylinders implanted in the corpora cavernosa of the penis.

In a two-piece inflatable penile prosthesis configuration, two inflatable penile cylinders are implanted in the corpora cavernosa of the penis. A multifunctional fluid reservoir, including fluid reservoir, fluid transfer system and cylinder deflate mechanism are implanted subcutaneously in the lower abdomen. Flexible tubing provides fluid communication between the inflatable penile cylinders, the fluid transfer system and the cylinder deflate mechanism incorporated in the multifunctional fluid reservoir. Using flexible tubing, the fluid transfer bulb and/or the deflate actuator bulb may be located remote from other components of the fluid transfer system and deflate mechanism respectively that are contained within the multifunctional reservoir. With either the fluid transfer bulb or deflate actuator bulb located remote from the multifunctional reservoir, the device might not be classified as a two-piece device.

In a three-piece inflatable penile prosthesis configuration, two inflatable penile cylinders are implanted in the corpora cavernosa of the penis. The fluid transfer system and deflate mechanism are combined into a unitary fluid transfer pump that is implanted in the scrotum. The fluid transfer system includes an inlet valve, an exhaust valve, and a spool valve assembly. The cylinder deflate mechanism has an integral deflate actuator button, a return valve and a spool valve assembly. A single spool valve assembly functions for both the fluid transfer system and deflate mechanism. A fluid reservoir is implanted in the abdomen, either in the Space of Retzius or subcutaneously in the lower abdomen. Flexible tubing provides fluid communication between the inflatable penile cylinders and the fluid reservoir placed in the abdomen to the fluid transfer pump placed in the scrotum.

Two-piece or three-piece inflatable penile prostheses described above may be provided as components that require assembly using tubing connectors by the surgeon at implantation or as fully assembled connector-less prostheses. Assembled devices may be provided unfilled or prefilled with physiological-type solution such as saline or radiopaque solutions. Devices may be provided either sterile or non-sterile. Sterile devices may be provided in packages having multiple barriers for presentation in a sterile field.

One embodiment is directed to an inflatable penile prosthesis (IPP) comprising a fluid reservoir, at least one inflatable penile cylinder, and a fluid transfer system in fluid communication with the fluid reservoir and with the at least one inflatable penile cylinder to inflate the at least one penile cylinder with fluid from the fluid reservoir. The fluid transfer system includes an inlet valve in fluid communication with the fluid reservoir, a fluid transfer bulb in fluid communication with the inlet valve, an exhaust valve in fluid communication with the fluid transfer bulb, and a spool valve assembly in fluid communication with the fluid transfer bulb and at least one inflatable penile cylinder. The IPP also includes a cylinder deflate mechanism in fluid communication with the fluid reservoir and with the at least one inflatable penile cylinder to return fluid from the at least one inflatable penile cylinder to the fluid reservoir. The cylinder deflate mechanism includes the spool valve assembly, a return valve in fluid communication with the reservoir and the at least one inflatable penile cylinder, and a deflate actuator arranged to shift the spool valve assembly to a cylinder deflate mode. The spool valve assembly can be shifted between a cylinder inflate mode and the cylinder deflate mode using a force external to the spool valve assembly.

Another embodiment is directed to a two-piece inflatable penile prosthesis (IPP) comprising a multifunctional fluid reservoir comprising a fluid transfer system to inflate the at least one penile cylinder and a cylinder deflate mechanism to return fluid from the at least one inflatable penile cylinder to the fluid reservoir. The fluid transfer system comprises an inlet valve in fluid communication with a fluid reservoir, a fluid transfer bulb in fluid communication with the inlet valve, an exhaust valve in fluid communication with the fluid transfer bulb, and a spool valve assembly in fluid communication with the fluid transfer bulb and the at least one inflatable penile cylinders. The cylinder deflate mechanism comprises the spool valve assembly, a return valve in fluid communication with the reservoir and the at least one inflatable penile cylinder, and a deflate actuator to shift the spool valve assembly to a cylinder deflate mode. At least one inflatable penile cylinder is in fluid communication with the multifunctional fluid reservoir. The spool valve assembly can be shifted between a cylinder inflate mode and the cylinder deflate mode using external force applied to a spool within the spool valve assembly.

Still another embodiment is directed to a three-piece implantable penile prosthesis (IPP) comprising a fluid reservoir, at least one inflatable penile cylinder in fluid communication with the fluid reservoir, and a fluid transfer pump in fluid communication with the fluid reservoir and with the at least one inflatable penile cylinder. The fluid transfer pump comprising a fluid transfer system and a deflate mechanism. The fluid transfer system comprises an inlet valve in fluid communication with the fluid reservoir, a fluid transfer bulb in fluid communication with the inlet valve, an exhaust valve in fluid communication with the fluid transfer bulb, and a spool valve assembly in fluid communication with the fluid transfer bulb and the at least one inflatable penile cylinder. The deflate mechanism comprises a spool valve assembly in fluid communication with the fluid reservoir and the at least one inflatable penile cylinder, a return valve in fluid communication with the reservoir and the at least one inflatable penile cylinder, and a deflate actuator button to mechanically shift the spool valve to a cylinder deflate mode. The spool valve assembly can be shifted between a cylinder inflate mode and the cylinder deflate mode using a force external to the spool valve assembly.

Yet another embodiment is directed to an inflatable penile prosthesis (IPP) comprising a fluid reservoir, at least one inflatable penile cylinder, a fluid transfer system to inflate the at least one penile cylinder with fluid from the fluid reservoir, and a deflate mechanism to return fluid from the at least one inflatable penile cylinder to the fluid reservoir. The fluid transfer system is positioned to provide fluid communication between the fluid reservoir and the at least one inflatable penile cylinder. The deflate mechanism is positioned to provide fluid communication between the fluid reservoir and the at least one inflatable penile cylinder. The fluid transfer system and the deflate mechanism include a shared spool valve assembly.

Another embodiment is directed to an inflatable penile prosthesis (IPP) comprising a fluid reservoir, at least one inflatable penile cylinder, and a fluid transfer system including a fluid transfer pump, a deflate mechanism and a shared spool valve assembly. The shared spool valve assembly comprises a housing with cylindrical bore and fluid ports associated with the fluid transfer system and the deflate mechanism and a spool capable of shifting axially within the housing to cooperate with the fluid ports in the housing. The spool includes a fluid transfer system channel, an exhaust valve located within the fluid transfer channel in the spool to prevent backflow from the at least one inflatable penile cylinder to the fluid transfer pump, a deflate mechanism fluid channel, and a return valve located within the deflate mechanism fluid channel in the spool to prevent backflow from the fluid reservoir to the at least one inflatable penile cylinder. The spool valve can be shifted between a cylinder inflate mode and a cylinder deflate mode using a force external to the spool valve.

Yet another embodiment is directed to an inflatable penile prosthesis (IPP) comprising a fluid reservoir having a substantially flat posterior base comprising a reinforced elastomeric base to maintain dimensional stability and at least one inflatable penile cylinder. A fluid transfer system inflates the at least one inflatable penile cylinder with fluid from the fluid reservoir. A deflate mechanism returns fluid from the at least one inflatable penile cylinder to the fluid reservoir.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

DETAILED DESCRIPTION

Figure 1:
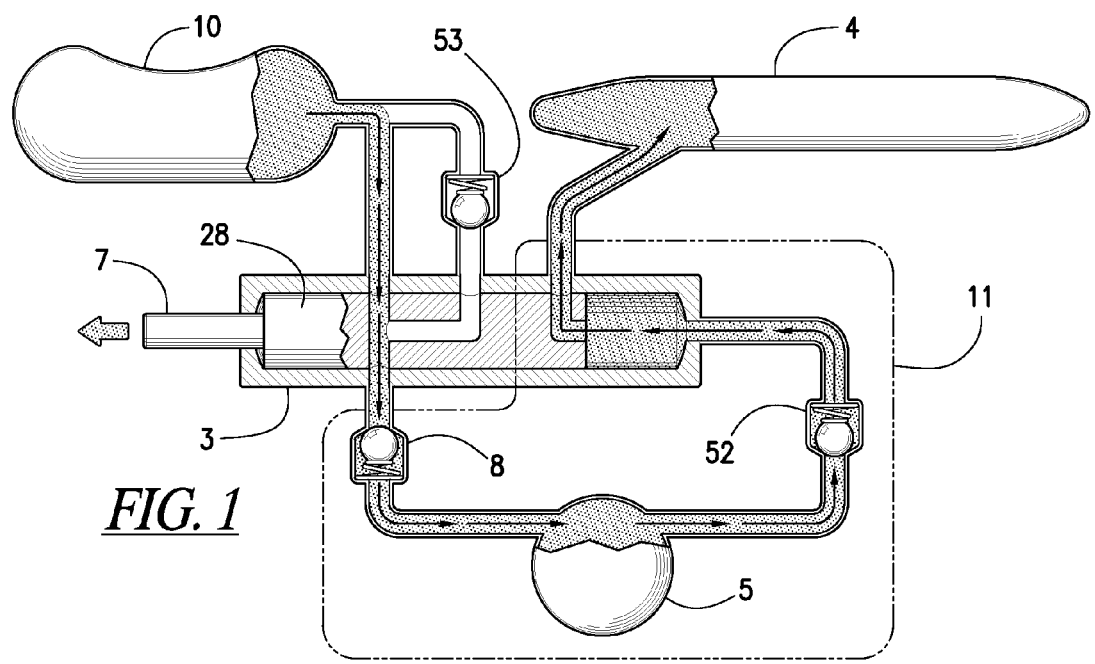
FIG. 1 is a schematic of an example implantable inflatable penile prosthesis incorporating a spool valve assembly depicted in a cylinder inflate mode according to one embodiment.

An implantable inflatable penile prosthesis (IPP) can be a unitary or multi-component device that is surgically implanted in a male patient to artificially achieve an erection of the penis for treatment of erectile dysfunction. IPP's operate hydraulically and may include at least one inflatable penile cylinder, a fluid reservoir that is in fluid communication with the at least one inflatable penile cylinder, a fluid transfer system to transfer fluid from the reservoir to the at least one inflatable penile cylinder, and a deflate mechanism for returning fluid from the at least one inflatable penile cylinder to the fluid reservoir.

The IPP can be operated in an inflate mode and in a deflate mode. In the inflate mode, also known as a cylinder inflate mode or device inflate mode, the cylinder or device inflates. The inflate mode is initiated by a volitional deformation of the fluid transfer bulb. Fluid from the fluid transfer bulb shifts the spool within the spool valve assembly to the inflate position. Once the spool is shifted to the inflate position, it remains in the inflate mode during recovery and repetitive deformation of the fluid transfer bulb, while the inflatable penile cylinders are filled and pressurized to the desired erectile state. Subsequent to operating the fluid transfer bulb, the spool valve assembly remains in the inflate mode until the spool is volitionally shifted to the deflate mode.

In the deflate mode, also known as a cylinder deflate mode or device deflate mode, the cylinder or device deflates. The deflate mode is initiated by the volitional actuation of either a deflate actuator button or a deflate actuator bulb. The deflate actuator applies force, either mechanical with the button or pilot pressure with the bulb, to shift the spool within the spool valve assembly to the deflate position. The spool remains in the deflate mode until it is volitionally shifted to the inflate position by deforming the fluid transfer bulb. In the deflate mode, fluid may return from the at least one inflatable cylinder through a return valve and a spool valve assembly to the reservoir until the desired penile flaccidity is achieved.

After the fluid transfer bulb or the deflate actuator bulb is deformed and the force to deform these bulbs is released, the bulbs rebound to their original shape during a phase known as recovery. During bulb recovery fluid is urged to refill the bulb due to a relatively sudden increase in volume or negative pressure within the bulb.

The IPP can be embodied as a two-piece IPP that can include two major components in fluid communication via flexible tubing, where the at least one inflatable penile cylinder is considered a single major component, regardless of whether one or two cylinders are used. The two major components include the at least one inflatable penile cylinder and a multifunctional fluid reservoir, including a fluid reservoir with an integral fluid transfer system and deflate mechanism. Alternately, the fluid transfer bulb and deflate actuator bulb may be located remote from the multifunctional reservoir.

The IPP can also be embodied as a three-piece IPP that includes three major components in fluid communication via flexible tubing, where the at least one inflatable penile cylinder is considered a single major component, regardless of whether one or two cylinders are used. The three major components include the at least one inflatable penile cylinder, the fluid reservoir and the fluid transfer pump with integral deflate mechanism.

The implantable inflatable penile prostheses described herein utilize inflatable penile cylinders, fluid transfer systems, deflate mechanisms and fluid storage reservoirs. The fluid transfer systems transfer fluid from the fluid storage reservoirs to the inflatable penile cylinders to cause penile erections. The deflate mechanisms provide a means to evacuate the fluid from the inflatable penile cylinders routing it to the fluid reservoirs.

A fluid transfer system is positioned to provide fluid communication between a fluid reservoir and inflatable penile cylinders. The fluid transfer system includes a spool valve assembly positioned to provide fluid communication between a fluid transfer bulb and inflatable penile cylinders.

A deflate mechanism is positioned to provide fluid communication between a fluid reservoir and inflatable penile cylinders. The deflate mechanism includes a spool valve assembly positioned to provide fluid communication between the fluid reservoir and the inflatable penile cylinders. The deflate mechanism may be actuated with an integral mechanical actuator such as a push button, or remotely actuated with pilot pressure from a deflate actuator bulb.

When the fluid transfer system and deflate mechanism are configured for a two-piece inflatable penile prosthesis they may be fabricated with individual components assembled so they are in fluid communication. The inlet valve, fluid transfer bulb, exhaust valve, spool valve assembly, return valve and deflate actuator may be separate components that are in fluid communication via flexible tubing. The deflate mechanism may be actuated with an integral mechanical actuator such as a push button, or remotely actuated with pilot pressure from a deflate actuator bulb. The fluid transfer bulb and deflate actuator bulb may be remotely located from other components of the fluid transfer system and deflate mechanism either within or externally remote to the multifunctional reservoir.

When the fluid transfer system and deflate mechanism are configured for a three-piece inflatable penile prosthesis they may be fabricated as a unitary fluid transfer pump consisting of an inlet valve, exhaust valve, fluid transfer bulb, spool valve assembly, return valve, deflate mechanism and deflate actuator button.

In an embodiment, the two-piece configuration features a multifunctional fluid reservoir consisting of fluid reservoir, inlet valve, exhaust valve, fluid transfer bulb, spool valve assembly, return valve and deflate mechanism. The deflate mechanism includes a spool valve assembly having a spool that may be shifted to the cylinder deflate position either with a mechanical actuator such as a push button or hydraulically by fluid pilot pressure from a remote source such as a deflate actuator bulb. Alternately, the fluid transfer bulb and/or deflate actuator bulb may be remote from the multifunctional reservoir, in fluid communication with the fluid transfer system and deflate mechanism via flexible tubing.

Application of pressure on the ends of the spool within the spool valve assembly shifts the spool to the desired position. During cylinder inflation, fluid from the fluid transfer bulb is directed to the end of the spool that shifts the spool to the cylinder inflate position. Force from the cylinder deflate actuator is directed to the end of the spool that shifts the spool to the cylinder deflate position. The force required to shift the spool valve to the cylinder deflate mode may be either a mechanical actuator button or fluid pressure from a deflate actuator bulb.

The spool valve assembly serves as a two-position directional valve without a neutral position. The spool valve either routes fluid from the fluid transfer bulb to the inflatable penile cylinders in the inflate mode or conversely, from the inflatable penile cylinders to the fluid reservoir in the cylinder deflate mode. One way check valves within the spool eliminate flow in the reverse direction; a return valve prevents fluid flow from the reservoir to the inflatable penile cylinders and an exhaust valve prevents fluid flow from the inflatable penile cylinders to the fluid transfer bulb.

Figure 2:
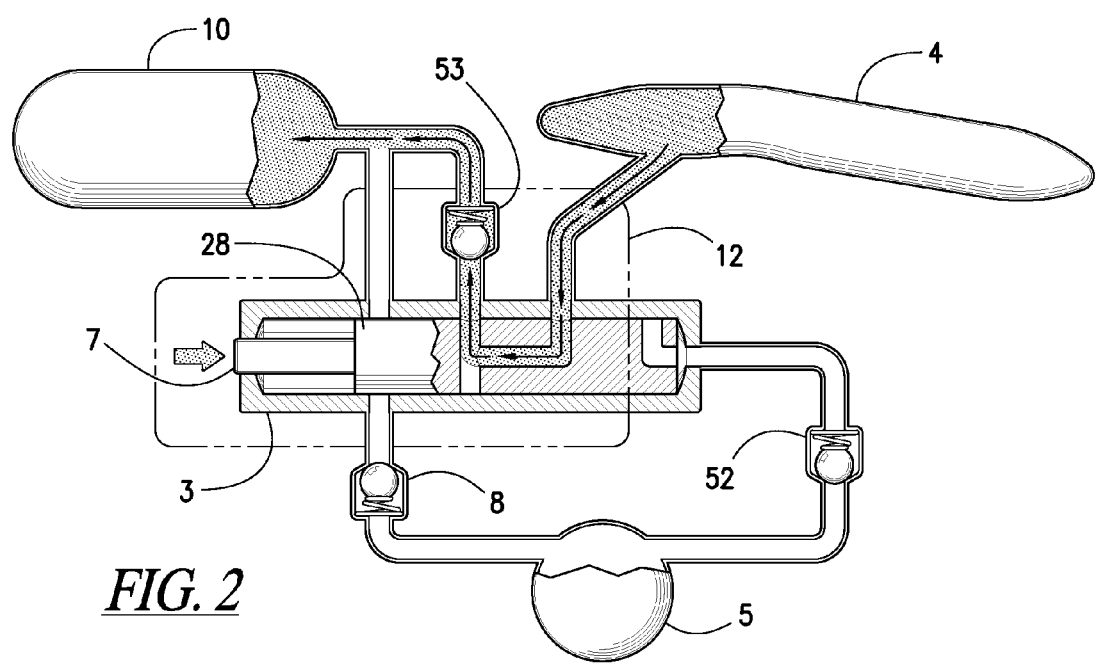
FIG. 2 is a schematic of the inflatable penile prosthesis of FIG. 1 with the spool valve assembly depicted in the cylinder deflate mode.

Referring now to the drawings, FIG. 1 schematically depicts an implantable inflatable penile prosthesis incorporating spool valve assembly 3 in an example configuration, fluid reservoir 10, at least one inflatable penile cylinder 4, fluid transfer system 11 and a deflate mechanism. Spool valve assembly 3, including deflate actuator button 7 and spool 28, is depicted in the cylinder inflate mode. Fluid transfer system 11 is comprised of inlet valve 8, fluid transfer bulb 5, exhaust valve 52 and spool valve assembly 3. This schematic depicts the fluid flow from reservoir 10 through fluid transfer system 11 to inflatable penile cylinder 4. FIG. 1 and FIG. 2 both depict inlet valve 8, exhaust valve 52 and return valve 53 as separate components that are not integrated into other components. In the preferred embodiment of a two-piece inflatable penile prosthesis, exhaust valve 52 and return valve 53 are integrated in spool 28 of spool valve assembly 3. In the preferred embodiment of a three-piece inflatable penile prosthesis, exhaust valve 52 and return valve 53 are integrated in spool 28 of spool valve assembly 3 and inlet valve 8 is incorporated with fluid transfer bulb 5 into fluid transfer pump 20 (not depicted in FIG. 1).

The spool valve assembly 3 may include a housing with cylindrical bore and fluid ports; housing end caps; a spool 28 with fluid ports, fluid channels and one or more valve chambers, the spool capable of shifting axially to cooperate with fluid ports in the housing; one or more spool end caps; exhaust valve 52 and return valve 53. The spool valve assembly 3 acts as a two-position directional valve that is volitionally shifted to the inflate or deflate modes using forces external to the spool valve. The spool valve can have exhaust and return valves within the spool to prevent fluid backflow through the spool valve assembly 3.

The inflatable penile cylinder 4 can include an elongated, hollow, elastomeric-type inflatable chamber or bladder affixed to a more rigid cylinder base, with tubing exiting the base for fluid communication with the fluid transfer system and deflate mechanism. The inflatable penile cylinder is implanted in the corpus cavernosum of the penis. The inflatable penile cylinder can have a distensible, non-distensible or limited distensibility chamber or bladder.

The exhaust valve 52 may be a normally closed one-way check valve located to provide fluid communication between the fluid transfer bulb 5 and the at least one inflatable penile cylinder 4. The exhaust valve is biased to prevent backflow of fluid from the at least one inflatable penile cylinder 4 to the fluid transfer bulb 5 when the fluid transfer bulb 5 recovers. A pressure differential caused by the deformation of the fluid transfer bulb 5 opens the exhaust valve 52, allowing fluid to flow from the fluid transfer bulb 5 to the at least one inflatable penile cylinder 4.

The return valve 53 is a normally closed one-way check valve that provides fluid communication between the at least one inflatable penile cylinder 4 and the fluid reservoir 10. The return valve is biased to prevent backflow of fluid from the reservoir 10 to the at least one inflatable penile cylinder 4. A pressure differential caused by the pressurization of the at least one inflatable penile cylinder 4 opens the return valve 53, allowing fluid to flow from the at least one inflatable penile cylinder 4 to the fluid reservoir 10. The return valve 53 can be located in a deflate mode fluid pathway within the spool 28 of the spool valve assembly 3.

The inlet valve 8 may be a normally closed one-way check valve to provide fluid communication between the reservoir 10 and the fluid transfer bulb 5 and can be biased to prevent backflow of fluid to the reservoir 10 when the fluid transfer bulb 5 is deformed. A pressure differential caused by the recovery of the fluid transfer bulb 5 acts to open the inlet valve 8 to admit fluid to refill the fluid transfer bulb 5.

The fluid transfer system 11 can include the inlet valve 8 located to provide fluid communication between the fluid reservoir 10 and the fluid transfer bulb 5, the fluid transfer bulb 5 located to provide fluid communication between the inlet valve 8 and the exhaust valve 52, the exhaust valve 52 located to provide fluid communication between the fluid transfer bulb 5 and the at least one inflatable penile cylinder 4, and a spool valve located to provide fluid communication between the fluid transfer bulb 5 and the at least one inflatable penile cylinder 4. The fluid transfer system components may be configured into a unitary fluid transfer pump component and can include a deflate mechanism. For example, a three-piece IPP having a fluid transfer system intended for implantation in the scrotum could be configured as a unitary pump component having an integral deflate mechanism. For a two-piece IPP, a fluid transfer system incorporated into a multifunctional reservoir could be configured with fluid transfer components in fluid communication via flexible tubing. The fluid transfer system is volitionally operated by the patient to achieve an artificial penile erection.

The fluid transfer bulb 5 may be implemented as an elastomeric bulb that can be volitionally deformed to exhaust fluid and recovers to refill with fluid when the force to deform it is removed. The fluid transfer bulb 5 may be configured as an integral part of a fluid transfer pump or an independent component of the fluid transfer system 11 connected to the inlet valve 8 and spool valve assembly 3 with flexible tubing.

FIG. 2 is a schematic of an implantable inflatable penile prosthesis incorporating spool valve assembly 3 in one example configuration, fluid reservoir 10, at least one inflatable penile cylinder 4, fluid transfer system and deflate mechanism 12. Spool valve assembly 3, including deflate actuator button 7 and spool 28, is depicted in the cylinder deflate mode. Deflate mechanism 12 is comprised of deflate actuator button 7, spool valve assembly 3 and return valve 53. This schematic depicts the fluid flow from cylinder 4 through the deflate mechanism 12 to reservoir 10.

The deflate mechanism 12 is volitionally actuated by the patient and returns the penis to a flaccid state. While the deflate mechanism 12 is depicted in FIG. 2 as including a deflate actuator button 7 that applies mechanical force, the deflate mechanism may alternatively utilize a deflate actuator bulb that applies hydraulic pilot pressure to shift the spool 28 within the spool valve assembly 3 to the deflate position. The spool 28 within the spool valve assembly 3 can include a return valve that allows fluid to flow from the at least one inflatable penile cylinder 4 to the fluid reservoir 10 when a pressure differential between the cylinder 4 and reservoir 10 is greater in the cylinder 4, and prevents backflow of fluid from the reservoir 10 to the cylinder 4 when the pressure differential between the cylinder 4 and the reservoir 10 is greater in the reservoir 10. The patient may reduce cylinder deflation time or achieve greater flaccidity by squeezing the penis to increase the pressure within the at least one inflatable penile cylinder 4 thereby increasing the pressure differential of the at least one inflatable penile cylinder 4 over the fluid reservoir 10. In a two-piece IPP, a deflate mechanism may be incorporated into a multifunctional fluid reservoir, where the spool valve assembly is contained within the reservoir. Either a deflate actuator button that is integral with spool valve assembly or a deflate actuator bulb that provides hydraulic pilot pressure and is fluidically connected to the spool valve assembly may be used to actuate the deflate mechanism. In a three-piece IPP the deflate mechanism may be incorporated with a fluid transfer system into a unitary fluid transfer pump implanted in the scrotum.

Figure 3:
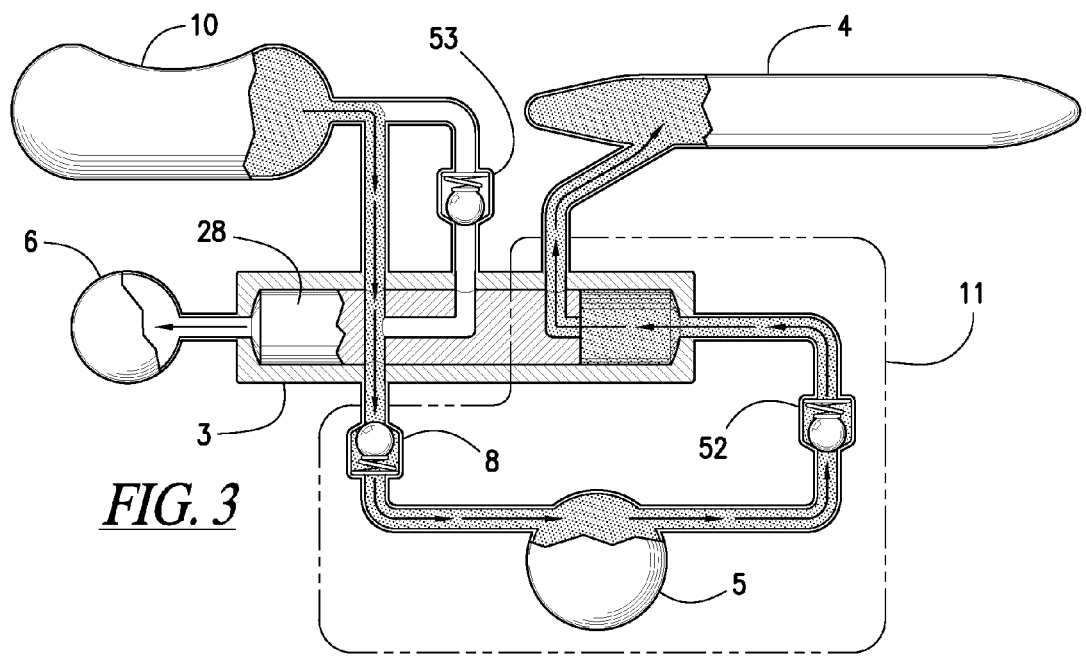
FIG. 3 is a schematic of another example implantable inflatable penile prosthesis incorporating a spool valve assembly depicted in the cylinder inflate mode according to another embodiment.
Figure 4:
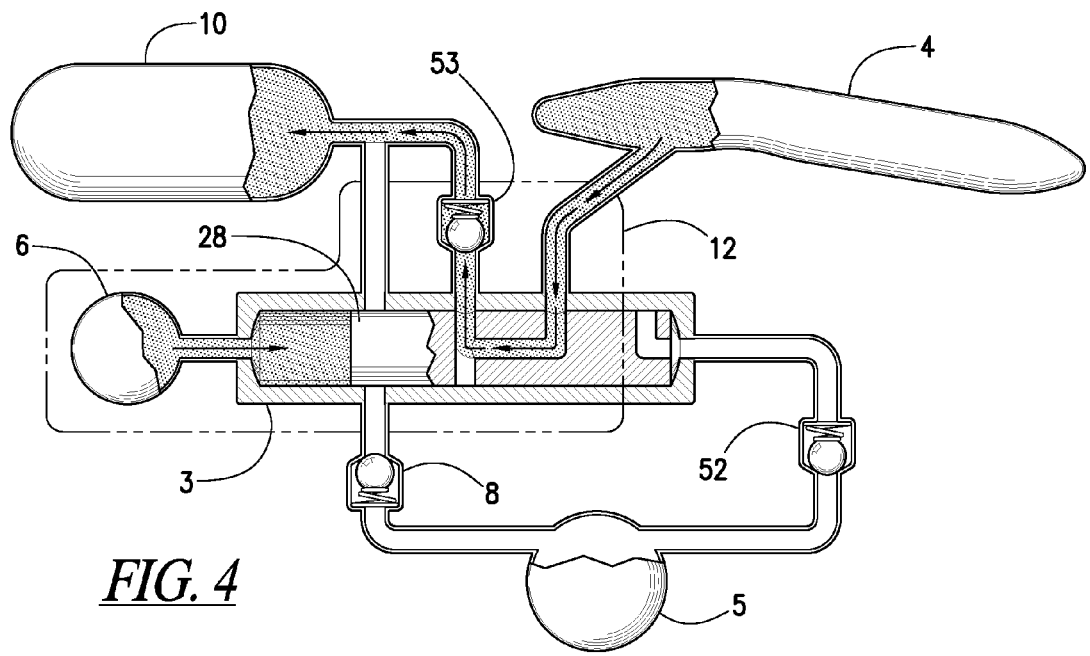
FIG. 4 is a schematic of the implantable inflatable penile prosthesis of FIG. 3 with the spool valve assembly depicted in the cylinder deflate mode.

FIG. 3 schematically depicts an implantable inflatable penile prosthesis incorporating spool valve assembly 3 in one example configuration, fluid reservoir 10, at least one inflatable penile cylinder 4, fluid transfer system 11 and a deflate mechanism with deflate actuator bulb 6. Spool valve assembly 3 with spool 28 is depicted in the cylinder inflate mode. Fluid transfer system 11 is comprised of inlet valve 8, fluid transfer bulb 5, exhaust valve 52 and spool valve assembly 3. This schematic depicts the fluid flow from reservoir 10 through fluid transfer system 11 to inflatable penile cylinder 4. FIG. 3 and FIG. 4 both depict inlet valve 8, exhaust valve 52 and return valve 53 as separate components that are not integrated into other components. In an example two-piece inflatable penile prosthesis embodiment, exhaust valve 52 and return valve 53 are integrated in spool 28 of spool valve assembly 3. In an example three-piece inflatable penile prosthesis embodiment, exhaust valve 52 and return valve 53 are integrated in spool 28 of spool valve assembly 3 and inlet valve 8 is incorporated with fluid transfer bulb 5 into fluid transfer pump 20 (not depicted in FIG. 3).

FIG. 4 is a schematic of an implantable inflatable penile prosthesis incorporating spool valve assembly 3 in one example configuration, fluid reservoir 10, at least one inflatable penile cylinder 4, a fluid transfer system and deflate mechanism 12. Spool valve assembly 3 with spool 28 is depicted in the cylinder deflate mode. Deflate mechanism 12 is comprised of deflate actuator bulb 6, spool valve assembly 3 and return valve 53. This schematic depicts the fluid flow from cylinder 4 through deflate mechanism 12 to reservoir 10.

Figure 5:
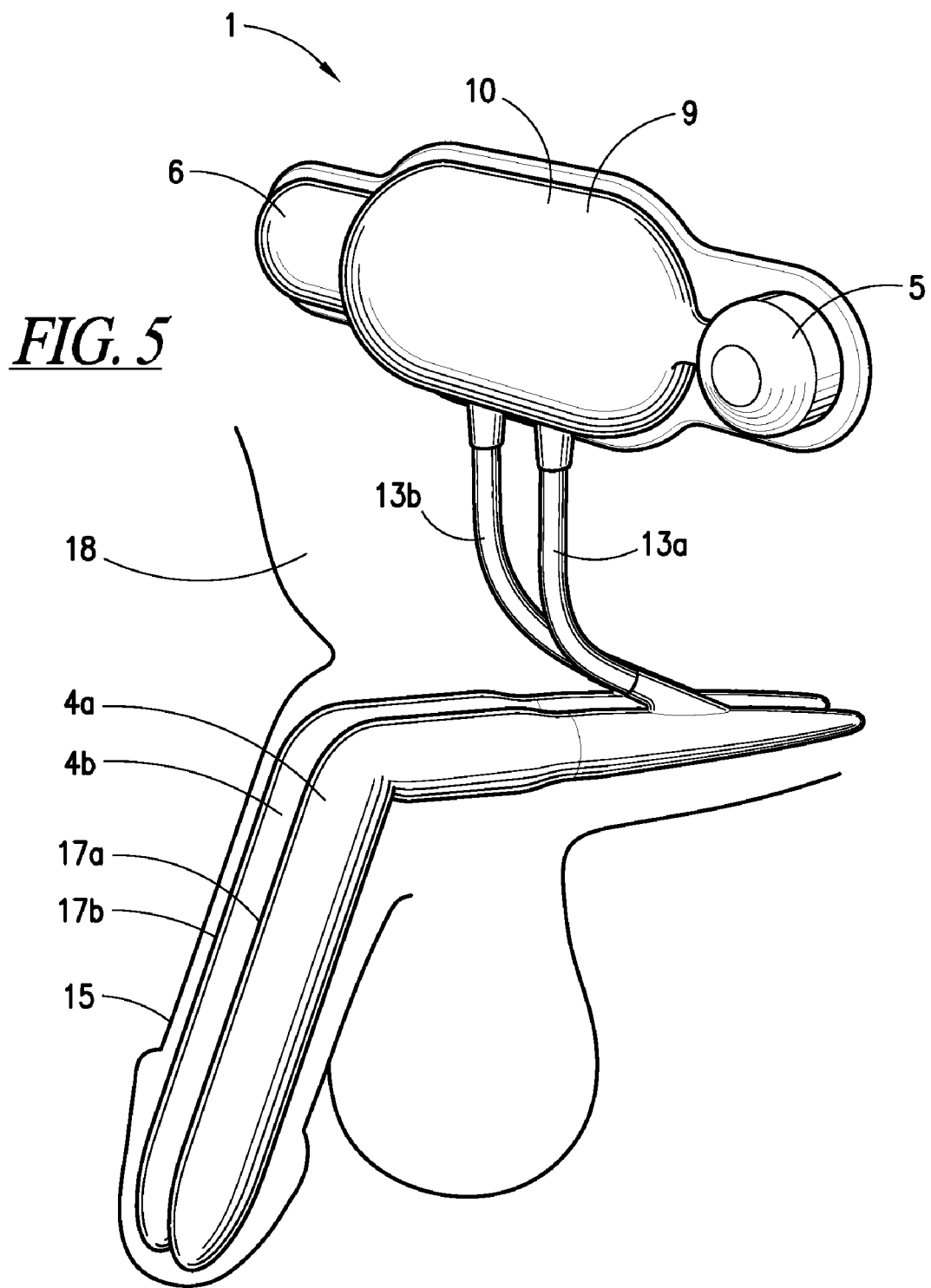
FIG. 5 depicts an implanted two-piece inflatable penile prosthesis in a flaccid state.

FIG. 5 depicts a two-piece inflatable penile prosthesis 1 with the penis 15 in the flaccid state. A multifunctional fluid reservoir 9 is implanted subcutaneously in the lower abdomen 18. The multifunctional fluid reservoir 9 may be fabricated from elastomeric material that conforms to the implant site and has a fluid chamber that collapses as fluid is removed. The multifunctional fluid reservoir 9 can incorporate multiple components into a unitary structure and may include, for example, fluid reservoir 10, integral fluid transfer system and cylinder deflate mechanism. Flexible elastomeric tubing provides fluid communication between the reservoir, fluid transfer system and deflate mechanism components. Flexible tubing 13a provides fluid communication between inflatable penile cylinder 4a implanted in corpus cavernosum 17a of penis 15 and multifunctional reservoir 9 implanted subcutaneously in lower abdomen 18. Flexible tubing 13b provides fluid communication between inflatable penile cylinder 4b implanted in corpus cavernosum 17b of penis 15 and multifunctional fluid reservoir 9 implanted subcutaneously in lower abdomen 18. Fluid transfer bulb 5 used to operate the fluid transfer system and deflate actuator bulb 6 used to actuate the cylinder deflate mechanism are located at the lateral extremities of multifunctional fluid reservoir 9. The inlet valve and spool valve assembly may be located within the reservoir.

Figure 6:
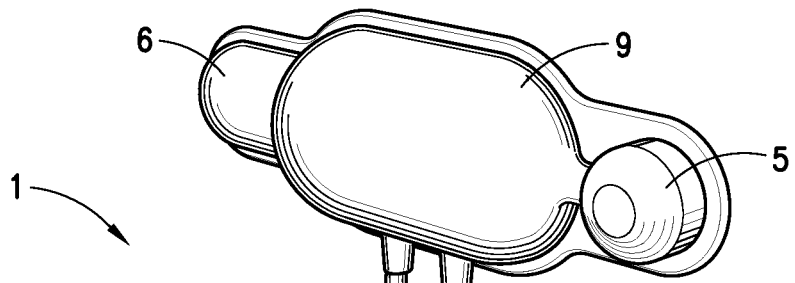
FIG. 6 depicts a two-piece inflatable penile prosthesis with multifunctional reservoir with the penile cylinders in the flaccid state.
Figure 6:
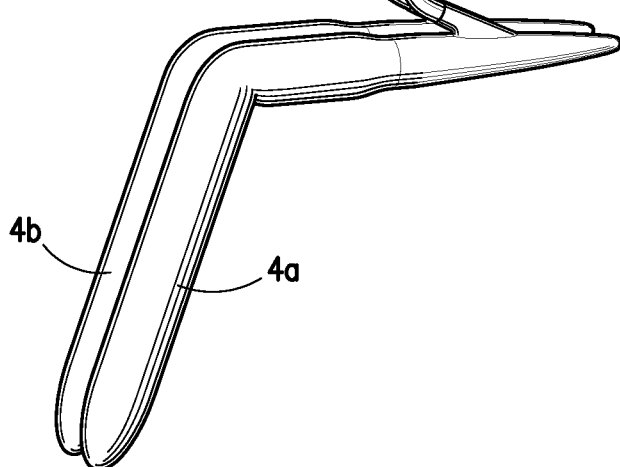

FIG. 6 depicts a two-piece inflatable penile prosthesis 1 with multifunctional fluid reservoir 9 and penile cylinders in the flaccid state. Multifunctional fluid reservoir 9 is substantially filled with fluid while the penile cylinders 4a and 4b are only partially filled with fluid. Fluid transfer bulb 5 operates the fluid transfer system and deflate actuator bulb 6 actuates cylinder deflate mechanism. Flexible tubing 13a and 13b provide fluid communication between inflatable penile cylinders 4a and 4b, respectively, to multifunctional fluid reservoir 9.

Figure 7:
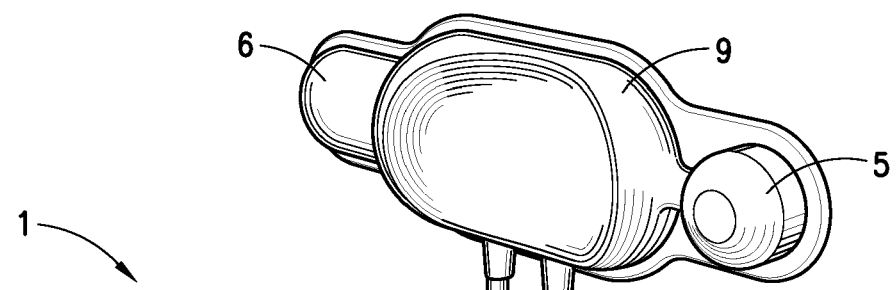
FIG. 7 depicts the two-piece inflatable penile prosthesis of FIG. 6 with the penile cylinders in the erectile state.
Figure 7:
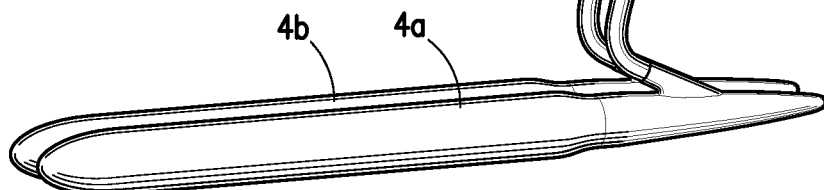

FIG. 7 depicts a two-piece inflatable penile prosthesis 1 with multifunctional fluid reservoir 9 and penile cylinders 4a and 4b in the erectile state. Multifunctional fluid reservoir 9 is partially filled with fluid while the inflatable penile cylinders 4a and 4b are substantially filled with fluid.

Figure 8:
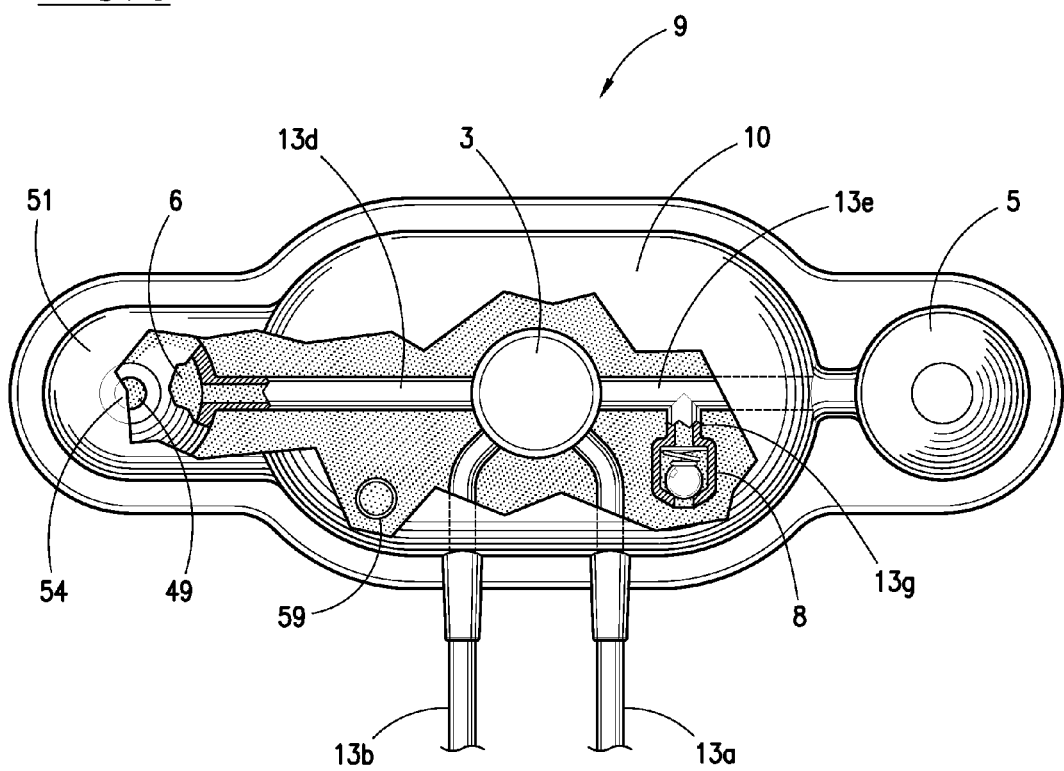
FIG. 8 depicts the multifunctional reservoir of FIG. 6 with the inlet valve, spool valve, fluid transfer bulb, deflate actuator bulb, fluid fill port and flexible tubing connecting the components exposed.

FIG. 8 depicts a multifunctional fluid reservoir 9 as depicted in FIGS. 6 and 7 with fluid reservoir 10 with anterior wall 51 opened to expose fluid fill port 59, inlet valve 8, spool valve assembly 3, fluid transfer bulb 5, deflate actuator bulb 6 and flexible tubing 13a, 13b, 13d, 13e and 13g. Deflate actuator bulb 6 has an aperture 49 through the apex of its dome that interacts with anterior wall 51 to comprise aperture valve 54. Fluid fill port 59 is used to fill and adjust device fluid volume either at the manufacturer, if the device is prefilled, or during surgical implantation. Fluid fill port 59 can be an injection-type port where the lumen or fluid chamber of reservoir 10 may be accessed via a sharp needle. An injection-type port has an elastomeric shell incorporating a plastic or metal needle guard to prevent punctures of the reservoir shell or base and a cavity filled with a self-sealing elastomer. Fluid fill port 59 may be an elastomeric valve-type port that accommodates a stylus that opens the valve to allow access to the reservoir chamber and closes when the stylus is removed. Fluid fill port 59 is bonded to either the shell or base and is located where it will be convenient to remove air from reservoir 10.

The fluid reservoir 10 can be used to store fluid for the IPP and would typically be implanted abdominally in the Space of Retzius or subcutaneously in the lower abdomen. The fluid reservoir 10 has an elastomeric bladder that collapses or deforms when fluid is withdrawn and returns to its normal shape as it fills with fluid. If the fluid reservoir 10 is a stand alone component, then it can have or be connected to a flexible tubing to provide fluid communication between it and the fluid transfer system, deflate mechanism and cylinders.

In one embodiment, a two-position spool valve assembly has a ported housing with a sliding spool, the sliding spool having fluid pathways that cooperate with housing ports to route fluid for inflating or evacuating inflatable penile cylinders. The spool has an internal exhaust valve chamber ported to provide fluid communication with the fluid transfer system, and the spool has an internal return valve chamber ported to provide fluid communication with a deflate mechanism. Incorporating the exhaust and return valves within the spool simplifies the device.

Figure 9:
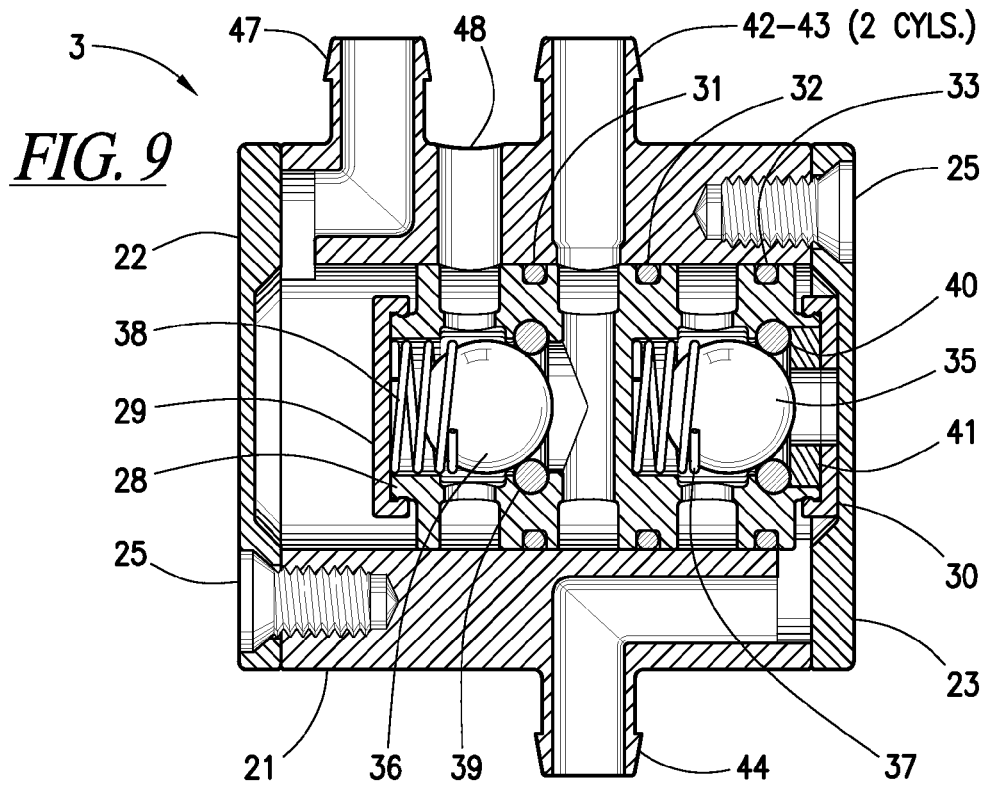
FIG. 9 is a sectional view of the spool valve used with a deflate actuator bulb depicted in FIG. 8, with the spool valve in the cylinder deflate mode.

FIG. 9 is a sectional view of spool valve assembly 3 used with deflate actuator bulb 6 depicted in FIG. 8, with the spool valve assembly 3 in the cylinder deflate mode. Spool valve assembly 3 includes valve housing 21, housing deflate end cap 22, housing inflate end cap 23, end cap screws 25, spool 28, spool deflate end cap 29, spool inflate end cap 30, o-rings 31, 32 and 33, balls 35 and 36, springs 37 and 38, valve seats 39 and 40, valve seat retainer 41 and cylinder spigots 42 and 43, transfer bulb spigot 44, deflate bulb spigot 47 and reservoir port 48.

Figure 10:
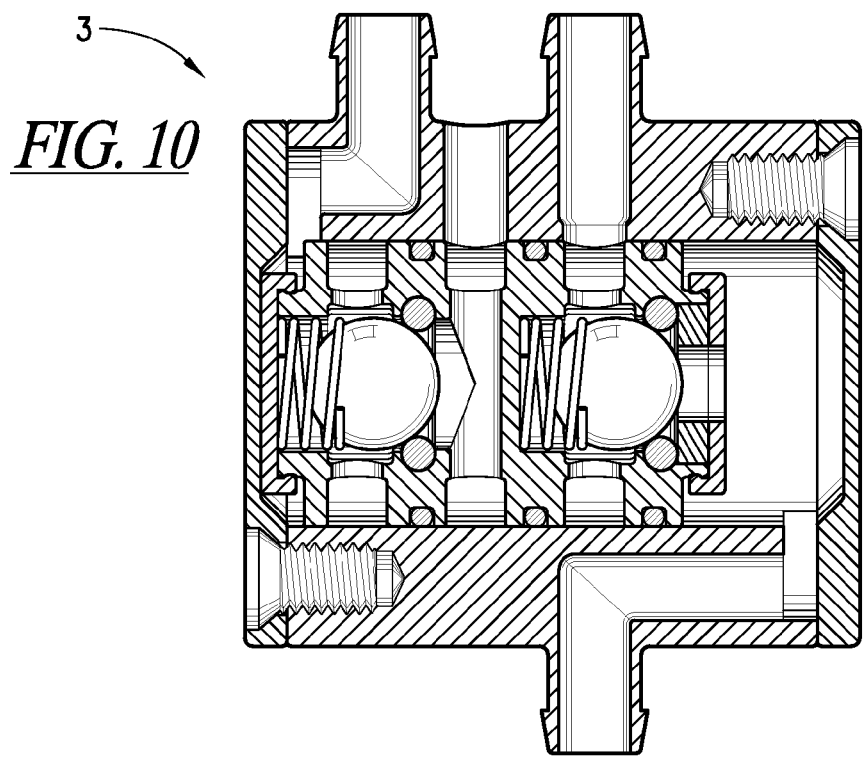
FIG. 10 is a sectional view of the spool valve used with a deflate actuator bulb depicted in FIG. 8, with the spool valve in the cylinder inflate mode.

FIG. 10 is a sectional view of the spool valve assembly 3 used with deflate actuator bulb 6 depicted in FIG. 8 with spool valve assembly 3 in the inflate mode.

Figure 11:
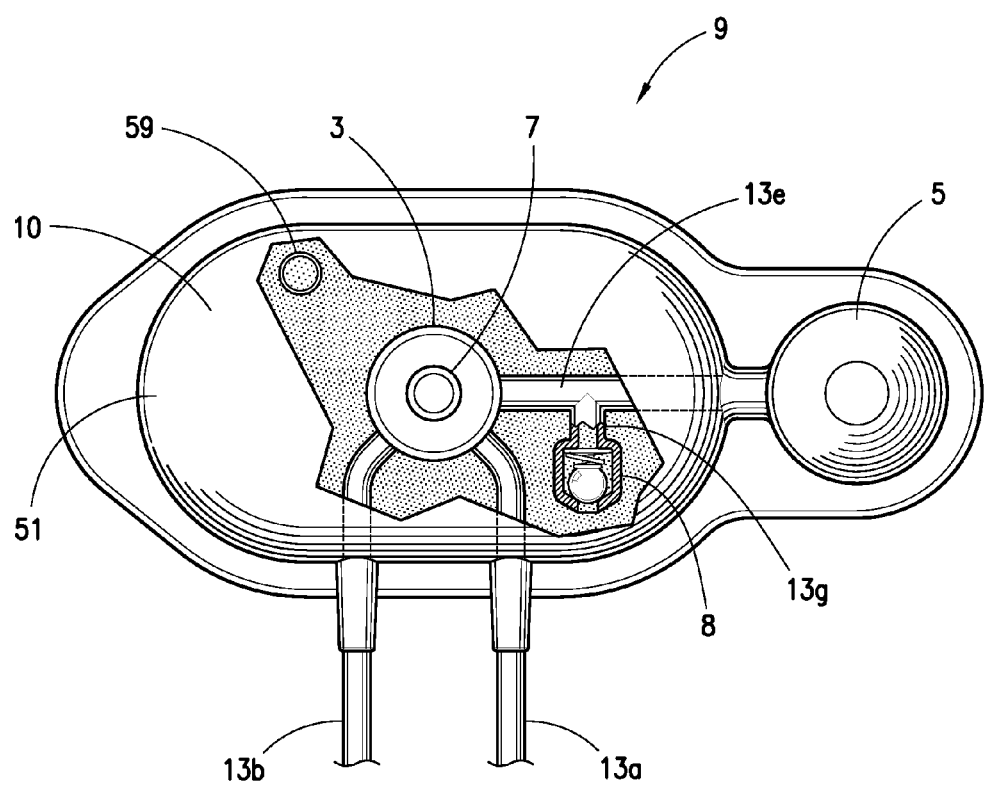
FIG. 11 depicts a multifunctional reservoir according to another embodiment, with the inlet valve, spool valve, fluid transfer bulb, deflate actuator button, fluid fill port and flexible tubing connecting the components exposed.

FIG. 11 depicts multifunctional reservoir 9 with fluid reservoir 10 with anterior wall 51 opened to expose fluid fill port 59, inlet valve 8, spool valve assembly 3, fluid transfer bulb 5, deflate actuator button 7 and flexible tubing 13a, 13b, 13e and 13g.

Figure 12:
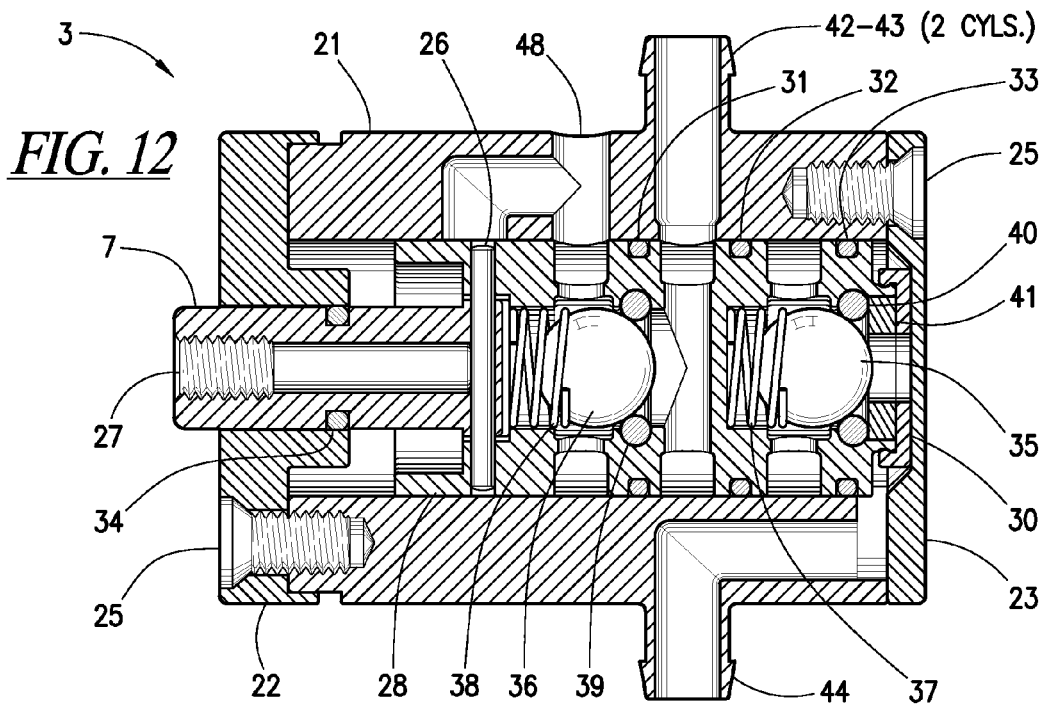
FIG. 12 is a sectional view of the spool valve used with a deflate actuator button depicted in FIG. 11, with the spool valve in the cylinder deflate mode.

FIG. 12 is a sectional view of spool valve assembly 3 used with a deflate actuator button 7 depicted in FIG. 11, with spool valve assembly 3 in the cylinder deflate mode. Spool valve assembly 3 includes valve housing 21, housing deflate end cap 22, housing inflate end cap 23, end cap screws 25, spool 28, spool inflate end cap 30, o-rings 31, 32, 33 and 34, balls 35 and 36, springs 37 and 38, valve seats 39 and 40, valve seat retainer 41 and cylinder spigots 42 and 43 and transfer bulb spigot 44, reservoir port 48, deflate actuator button 7, deflate button pin 26, and deflate button screw 27.

Figure 13:
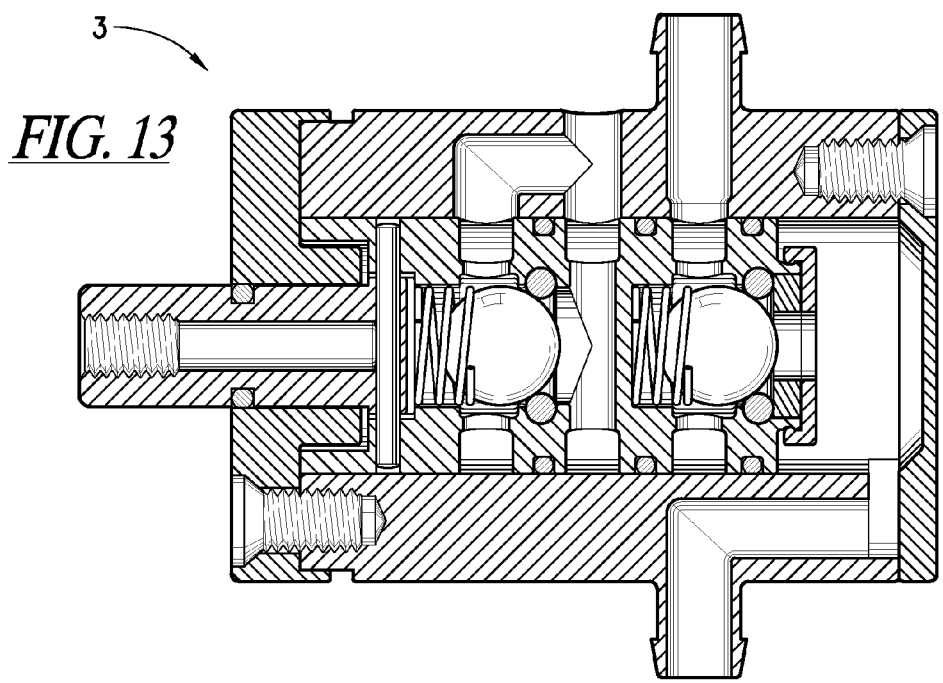
FIG. 13 is a sectional view of the spool valve used with a deflate actuator button depicted in FIG. 11, with the spool valve in the cylinder inflate mode.

FIG. 13 is a sectional view of the spool valve assembly 3 used with deflate actuator button 7 depicted in FIG. 11, with spool valve assembly 3 in the inflate mode.

Figure 14:
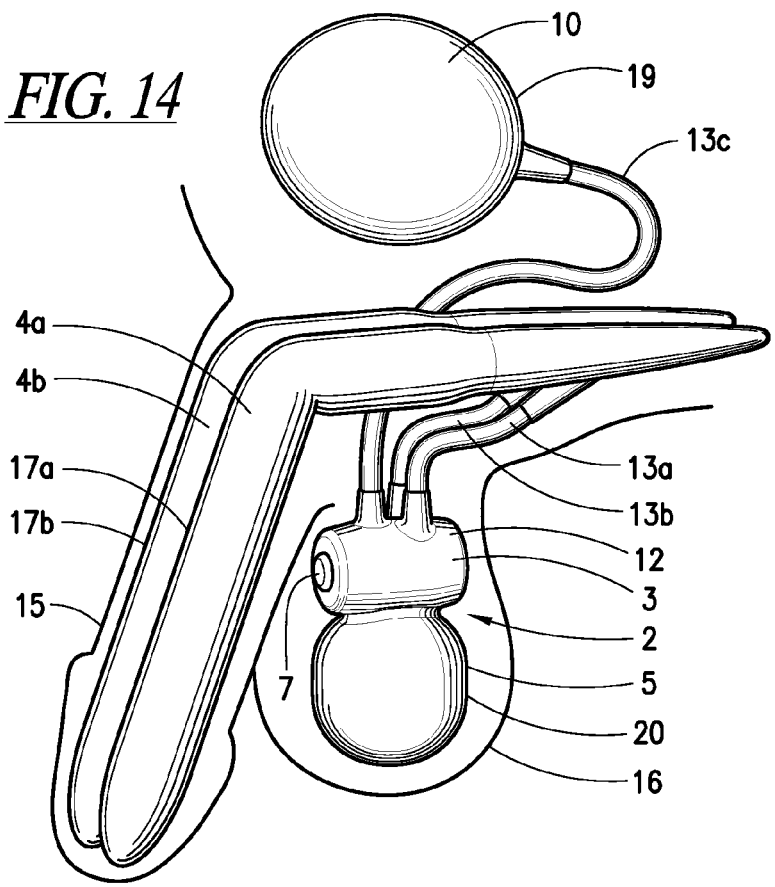
FIG. 14 depicts an example implanted three-piece inflatable penile prosthesis in the flaccid state according to one embodiment.

FIG. 14 depicts an implanted three-piece inflatable penile prosthesis 2 in the flaccid state. Fluid reservoir 10 is implanted in the abdominal Space of Retzius 19. Fluid transfer pump 20 with spool valve assembly 3 and integral deflate mechanism 12, including deflate actuator button 7, is implanted in scrotum 16. Inflatable penile cylinders 4a and 4b are implanted in the corpus cavernosa 17a and 17b, respectively, of the penis 15. Flexible tubing 13a and 13b fluidically connect penile cylinders 4a and 4b respectively and fluid transfer pump 20. Flexible tubing 13c connects fluid reservoir 10 and fluid transfer pump 20. FIG. 14 depicts spool valve assembly 3 configured with its central axis perpendicular to the central axis of fluid transfer bulb 5.

The fluid transfer pump 20 may include a fluid transfer system and deflate mechanism that are configured into a single fluid transfer pump with the fluid transfer system including an inlet valve, fluid transfer bulb, exhaust valve and spool valve assembly and the deflate mechanism including a deflate button actuator, spool valve assembly and return valve.

Figure 15:
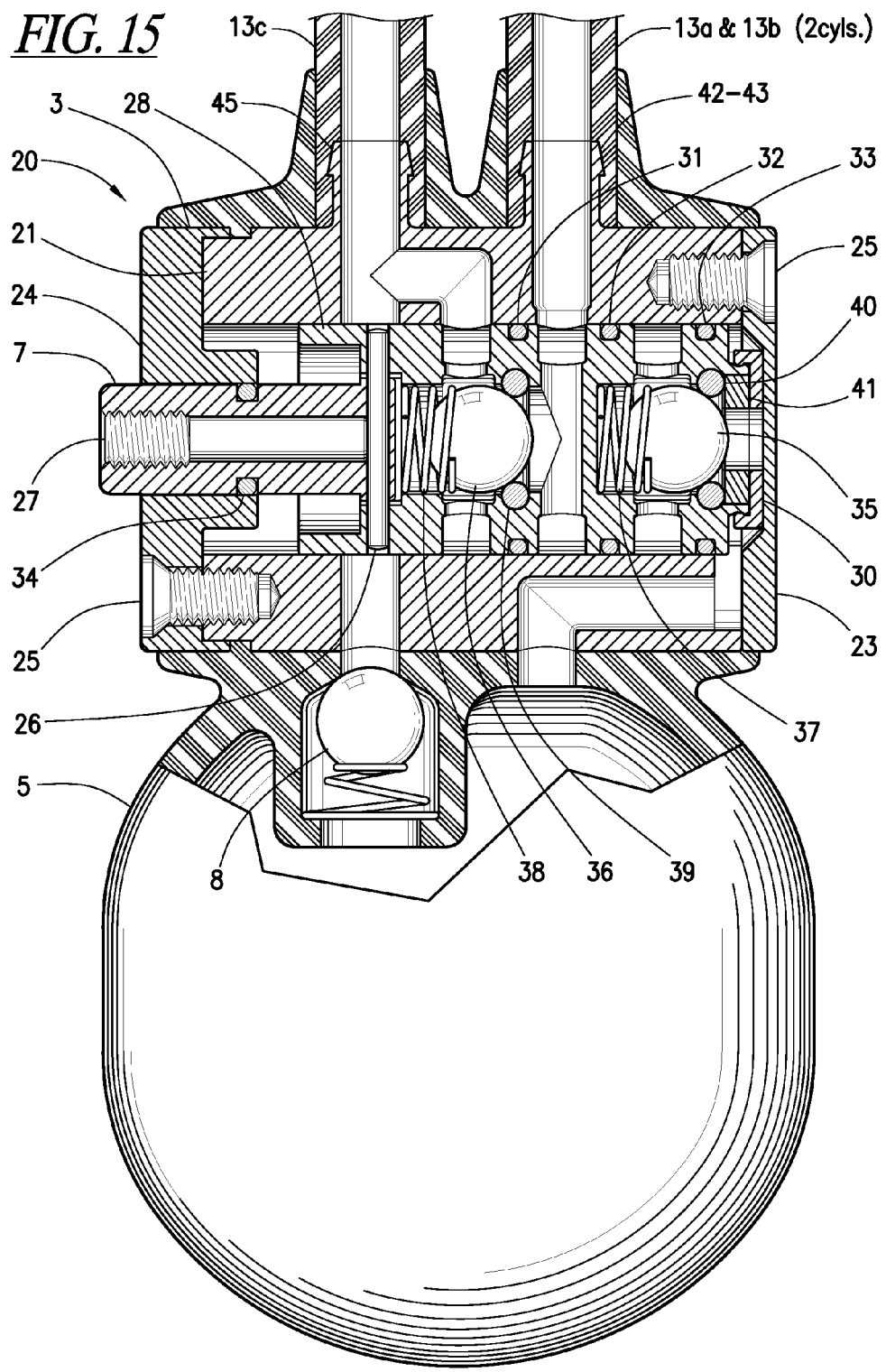
FIG. 15 is a cross-sectional view of the fluid transfer pump with integral cylinder deflate mechanism with the spool valve in the cylinder deflate mode as depicted in FIG. 14.

FIG. 15 is a sectional view of fluid transfer pump 20 with fluid transfer bulb 5, inlet valve 8, integral deflate mechanism 12 (illustrated in FIG. 2) with the spool valve assembly 3 in the cylinder deflate mode as depicted in FIG. 14. Spool valve assembly 3 includes valve housing 21, housing deflate end cap 24, housing inflate end cap 23, end cap screws 25, deflate actuator button 7, deflate button screw 27, deflate button pin 26, spool 28, spool inflate end cap 30, o-rings 31, 32, 33 and 34, balls 35 and 36, springs 37 and 38, valve seats 39 and 40, valve seat retainer 41 and cylinder spigots 42 and 43 and reservoir spigot 45.

Figure 16:
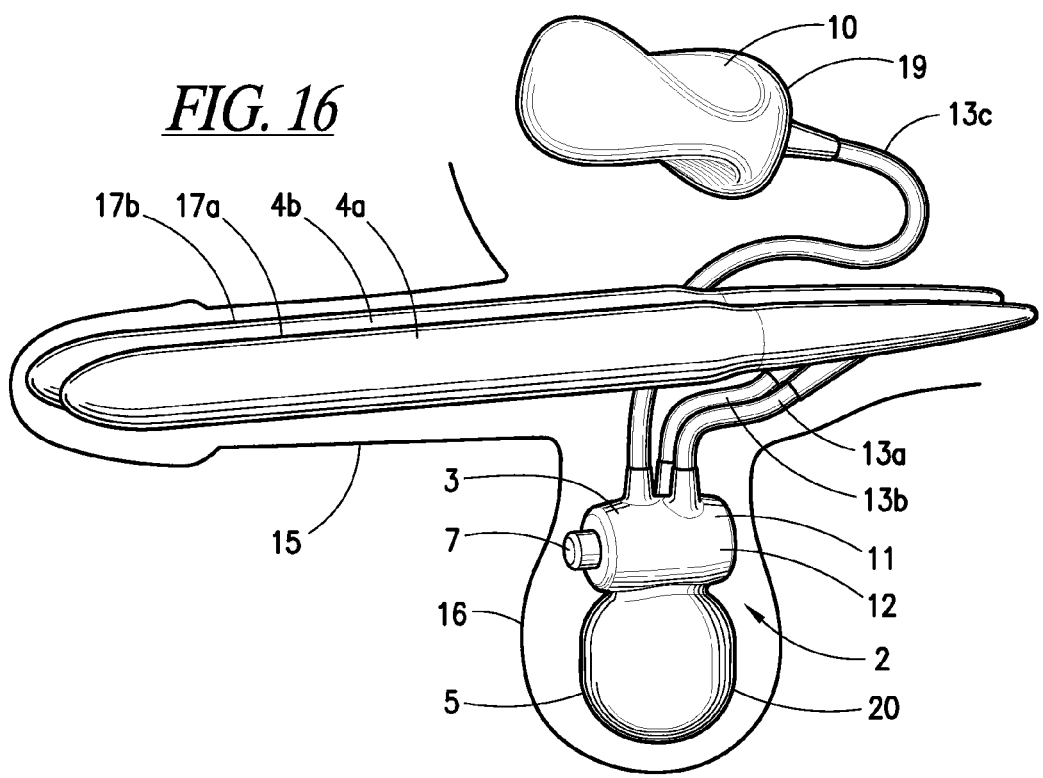
FIG. 16 depicts the implanted three-piece piece inflatable penile prosthesis of FIG. 14 in the erectile state.

FIG. 16 depicts an implanted three-piece piece inflatable penile prosthesis 2 in the erectile state. Fluid reservoir 10 is implanted in the abdominal Space of Retzius 19. Fluid transfer pump 20 with spool valve assembly 3 includes fluid transfer system 11, integral deflate mechanism 12 with deflate actuator button 7, that is implanted in scrotum 16. Inflatable penile cylinders 4a and 4b are implanted in the corpus cavernosa 17a and 17b, respectively, of the penis 15. Flexible tubing 13a and 13b provide fluid communication between penile cylinders 4a and 4b, respectively, and fluid transfer pump 20. Flexible tubing 13c connects fluid reservoir 10 and fluid transfer pump 20.

Figure 17:
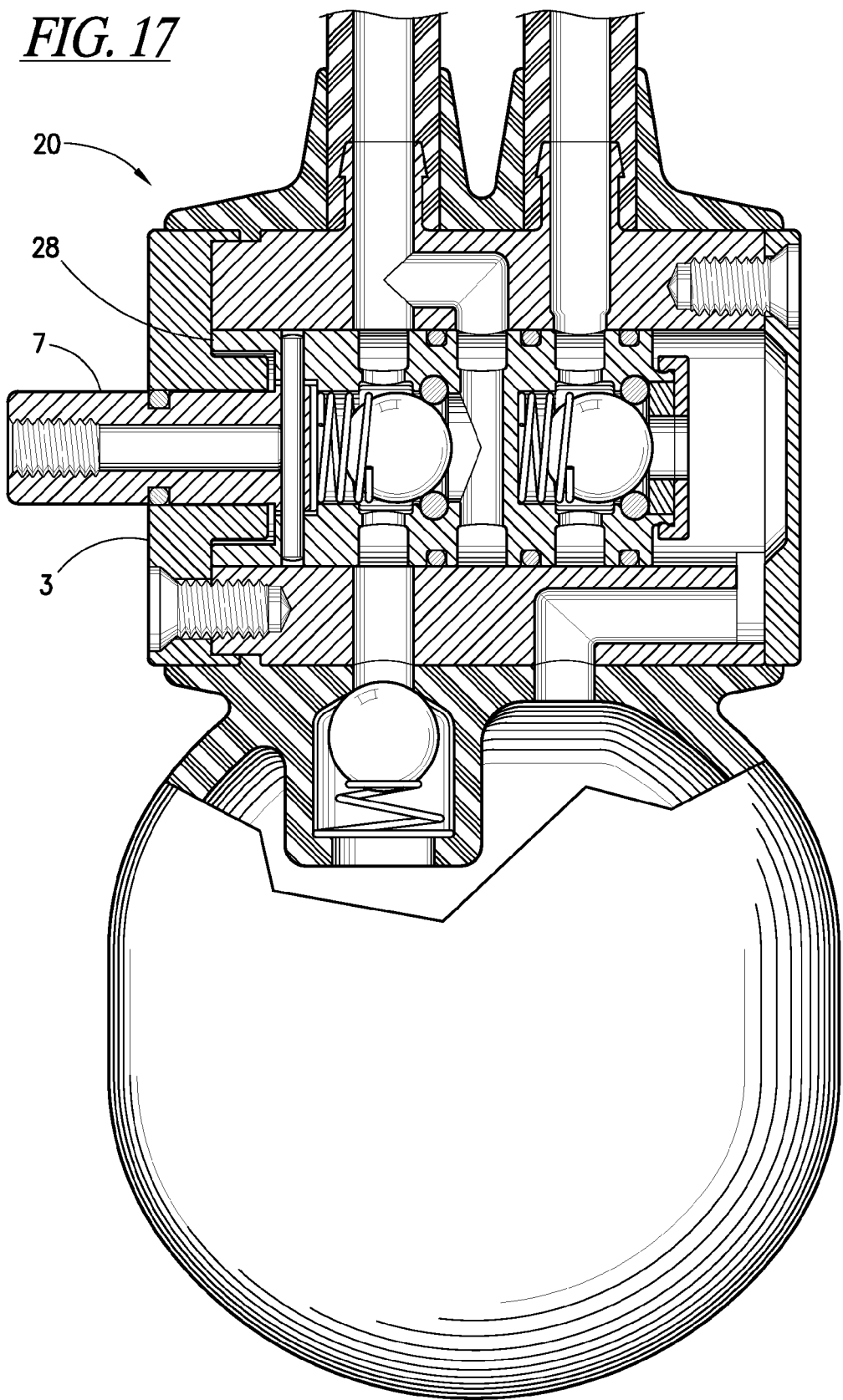
FIG. 17 is a sectional view of the fluid transfer pump with integral cylinder deflate mechanism with the spool valve assembly in the cylinder inflate mode as depicted in FIG. 16.

FIG. 17 is a sectional view of the fluid transfer pump 20 as depicted in FIG. 16 with the spool valve assembly 3 in the cylinder inflate mode.

Figure 18:
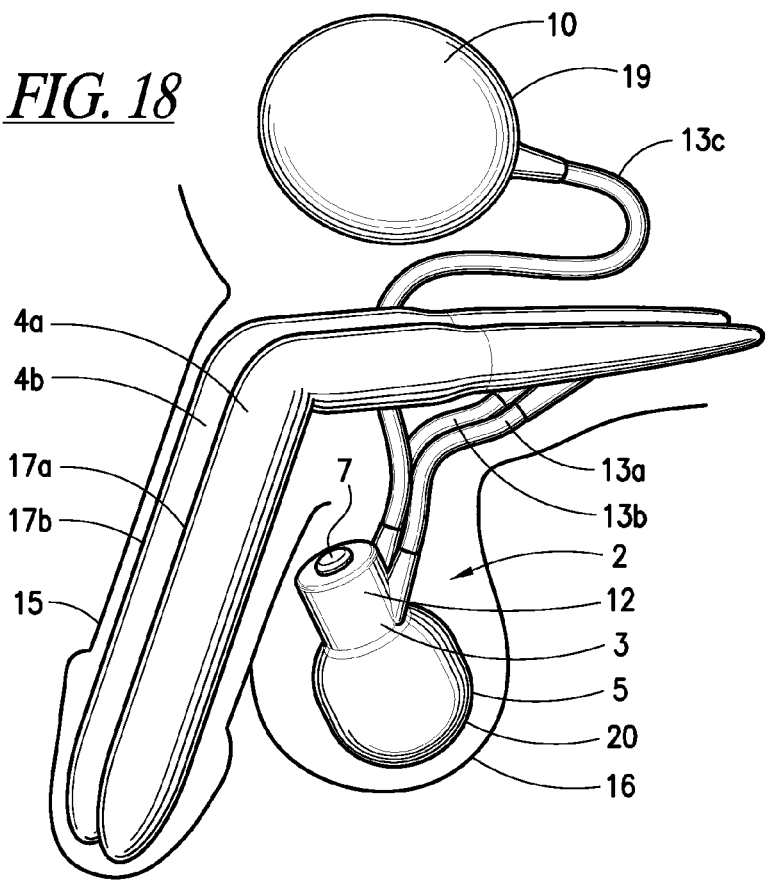
FIG. 18 depicts an example implanted three-piece inflatable penile prosthesis in the flaccid state.

FIG. 18 depicts an implanted three-piece inflatable penile prosthesis 2 in the flaccid state. Fluid reservoir 10 is implanted in the abdominal Space of Retzius 19. Fluid transfer pump 20 with spool valve assembly 3 and integral deflate mechanism 12, including deflate actuator button 7, is implanted in scrotum 16. Inflatable penile cylinders 4a and 4b are implanted in the corpus cavernosa 17a and 17b, respectively, of the penis 15. Flexible tubing 13a and 13b provide fluid communication between penile cylinders 4a and 4b, respectively, and fluid transfer pump 20. Flexible tubing 13c connects fluid reservoir 10 and fluid transfer pump 20. FIG. 18 depicts spool valve assembly 3 configured with its central axis corresponding to the central axis of fluid transfer bulb 5.

Figure 19:
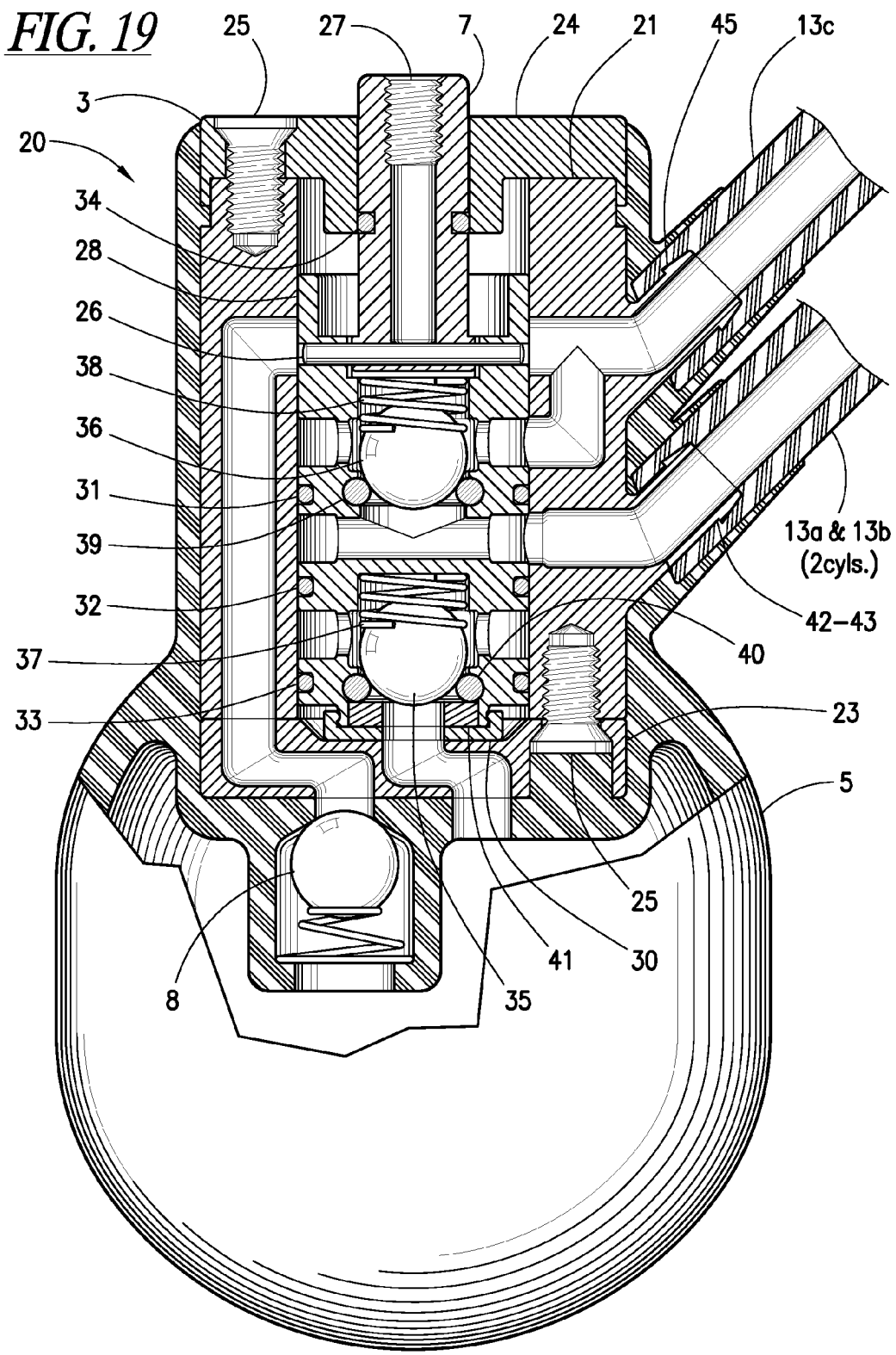
FIG. 19 is a cross-sectional view of the fluid transfer pump with integral cylinder deflate mechanism with the spool valve in the cylinder deflate mode as depicted in FIG. 18.

FIG. 19 is a sectional view of fluid transfer pump 20 with inlet valve 8, integral deflate mechanism 12 (depicted in FIG. 2) with the spool valve assembly 3 in the cylinder deflate mode as depicted in FIG. 18. Spool valve assembly 3 includes valve housing 21, housing deflate end cap 24, housing inflate end cap 23, end cap screws 25, deflate actuator button 7, deflate button screw 27, deflate button pin 26, spool 28, spool inflate end cap 30, o-rings 31, 32, 33 and 34, balls 35 and 36, springs 37 and 38, valve seats 39 and 40, valve seat retainer 41 and cylinder spigots 42 and 43 and reservoir spigot 45.

Figure 20:
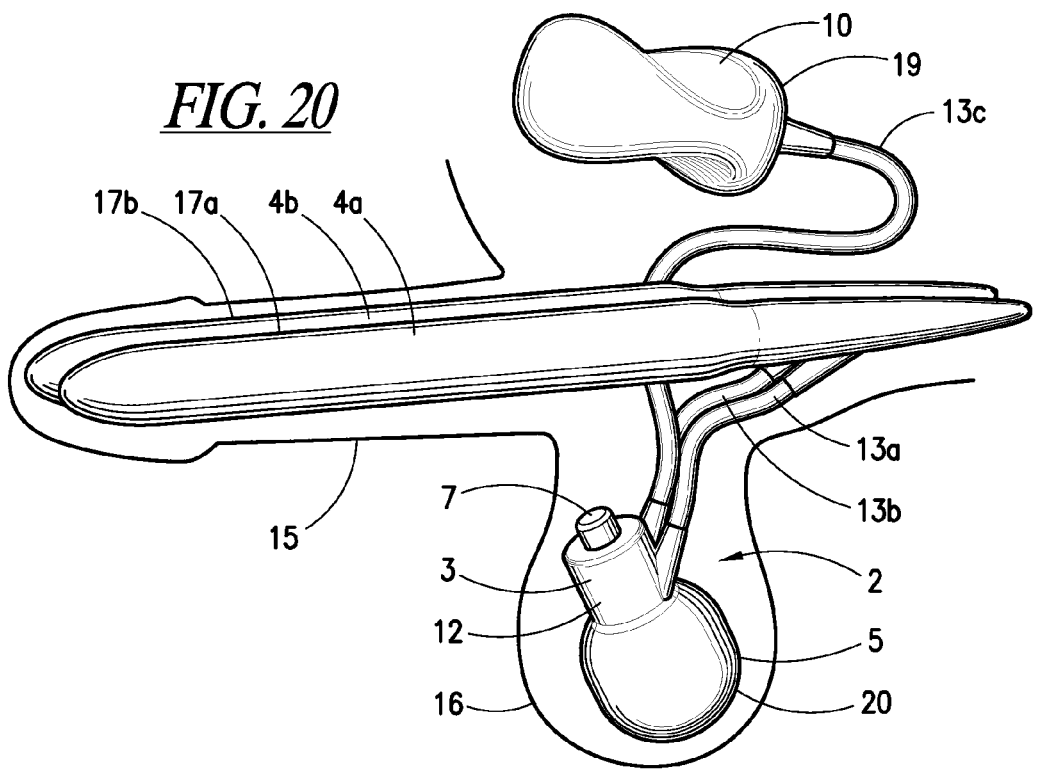
FIG. 20 depicts the implanted three-piece piece inflatable penile prosthesis of FIG. 18 in the erectile state.

FIG. 20 depicts an implanted three-piece piece inflatable penile prosthesis 2 in the erectile state. Fluid reservoir 10 is implanted in abdominal Space of Retzius 19. Fluid transfer pump 20 with spool valve assembly 3 and integral deflate mechanism 12, including deflate actuator button 7, is implanted in the scrotum 16. Inflatable penile cylinders 4a and 4b are implanted in the corpus cavernosa 17a and 17b, respectively, of the penis 15. Flexible tubing 13a and 13b provide fluid communication between penile cylinders 4a and 4b, respectively, and fluid transfer pump 20. Flexible tubing 13c connects fluid reservoir 10 and fluid transfer pump 20. FIG. 20 depicts spool valve assembly 3 configured with its central axis corresponding to the central axis of fluid transfer bulb 5.

Figure 21:
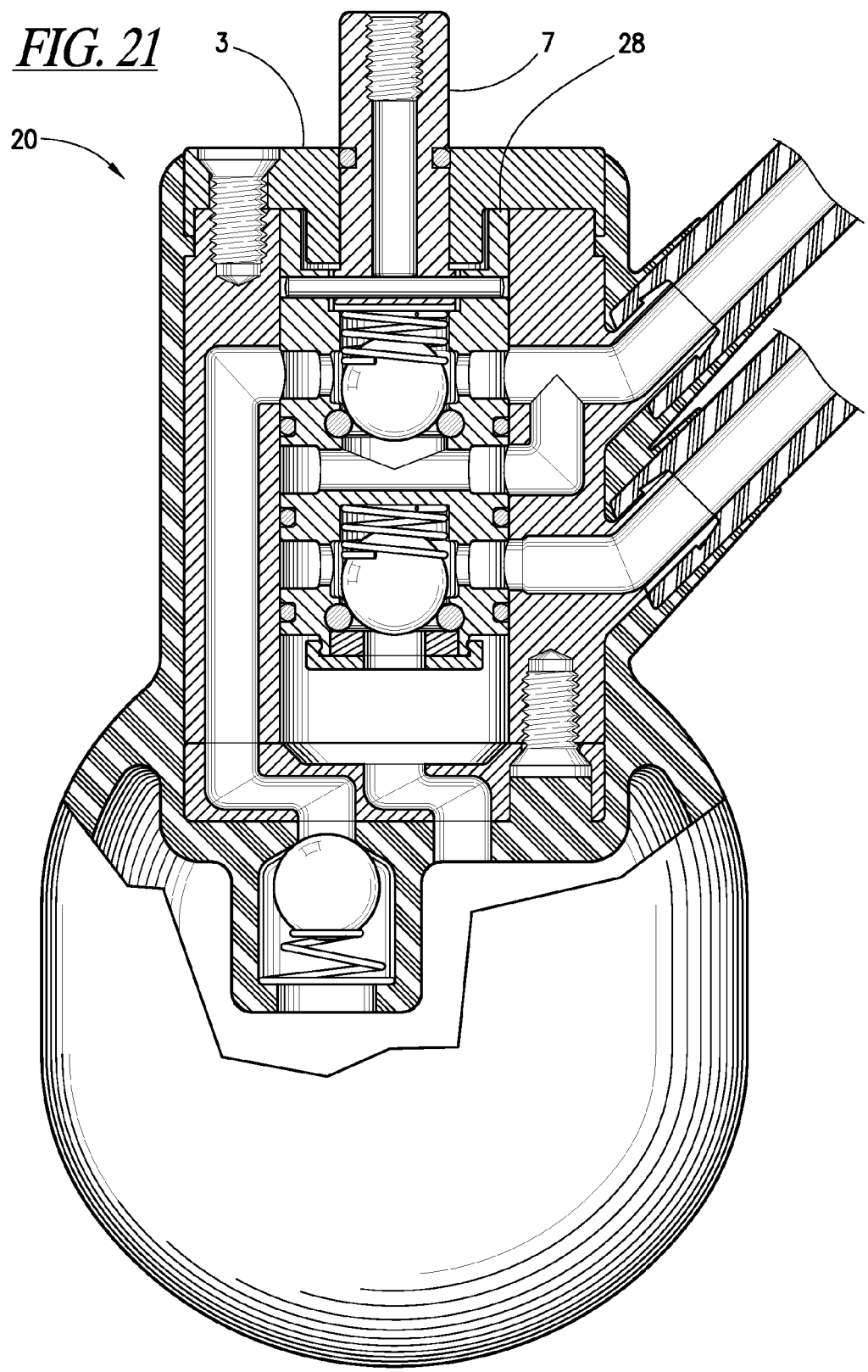
FIG. 21 is a cross-sectional view of the fluid transfer pump with integral cylinder deflate mechanism with the spool valve assembly in the cylinder inflate mode as depicted in FIG. 20.

FIG. 21 is a sectional view of the fluid transfer pump 20 depicted in FIG. 20 with the spool valve assembly 3 in the cylinder inflate mode.

Figure 22:
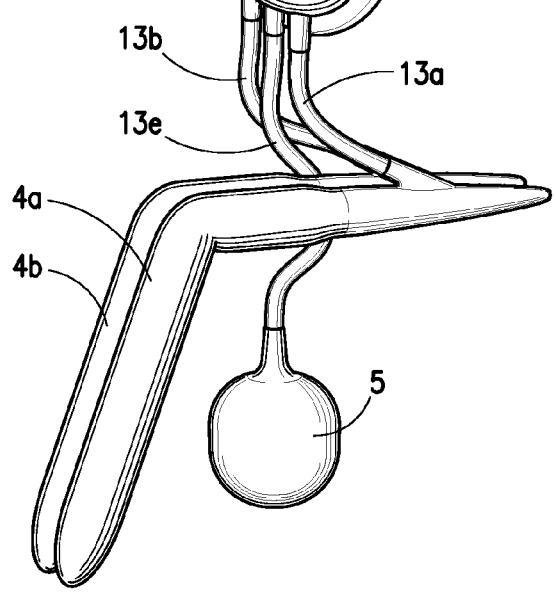
FIG. 22 depicts an example inflatable penile prosthesis with a substantially round multifunctional reservoir, remote fluid transfer bulb and penile cylinders according to another embodiment in the flaccid state.

FIG. 22 depicts a three-piece inflatable penile prosthesis 55 of the present invention with substantially round multifunctional fluid reservoir 9, cylinders 4a and 4b in the flaccid state, and fluid transfer bulb 5 in fluid communication via flexible tubing 13e with other components (not depicted) comprising the fluid transfer system that are contained within multifunctional reservoir 9. Fluid transfer bulb 5 operates the fluid transfer system and deflate actuator button 7 actuates the cylinder deflate mechanism (not depicted). Flexible tubing 13a and 13b provide fluid communication between inflatable penile cylinders 4a and 4b, respectively, to multifunctional reservoir 9.

Figure 23:
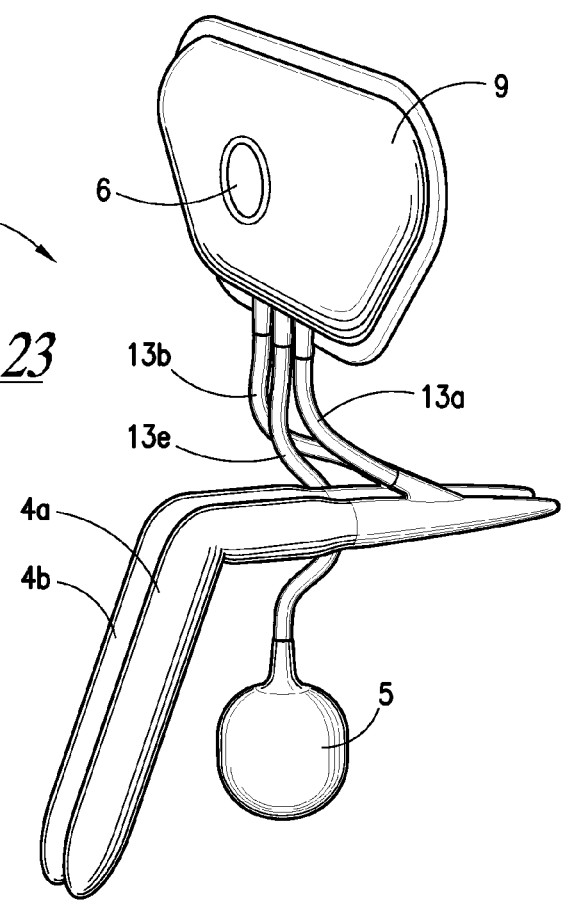
FIG. 23 depicts an example inflatable penile prosthesis with a substantially four-sided multifunctional reservoir, remote fluid transfer bulb and penile cylinders according to still another embodiment in the flaccid state.

FIG. 23 depicts an example three-piece inflatable penile prosthesis 55 with substantially four-sided multifunctional fluid reservoir 9, cylinders 4a and 4b in the flaccid state, and fluid transfer bulb 5 in fluid communication via flexible tubing 13e with other components (not depicted) comprising the fluid transfer system that are contained within multifunctional reservoir 9. Fluid transfer bulb 5 operates the fluid transfer system and deflate actuator bulb 6 actuates the cylinder deflate mechanism (not depicted). Flexible tubing 13a and 13b provide fluid communication between inflatable penile cylinders 4a and 4b, respectively, to multifunctional reservoir 9.

Figure 24:
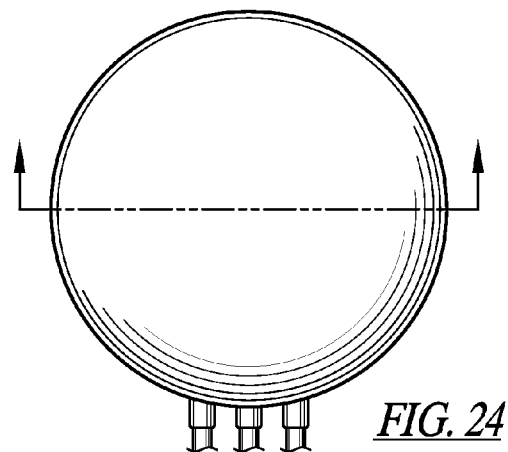
FIG. 24 depicts a substantially round multifunctional reservoir with three flexible tubing segments emanating from the reservoir.
Figure 24A:
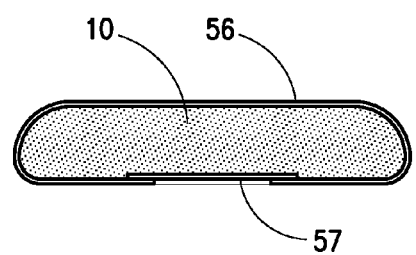
FIG. 24a is a cross-sectional view of the reservoir bladder depicted in FIG. 24 showing the configuration of a reservoir shell with a patch closure, without the other components.
Figure 25:
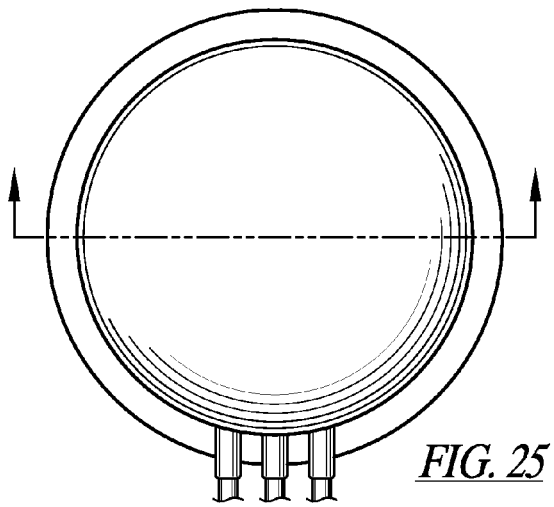
FIG. 25 depicts a substantially round multifunctional reservoir with three flexible tubing segments emanating from the reservoir.
Figure 25A:
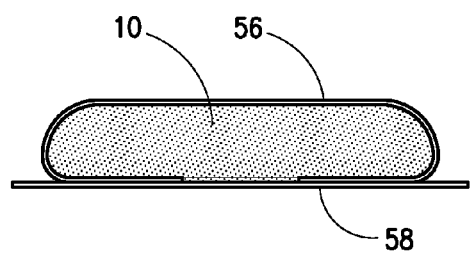
FIG. 25a is a cross-sectional view of the reservoir bladder depicted in FIG. 25 showing the configuration of a reservoir shell secured to a base, without the other components. The base extends peripherally beyond the reservoir shell.
Figure 26:
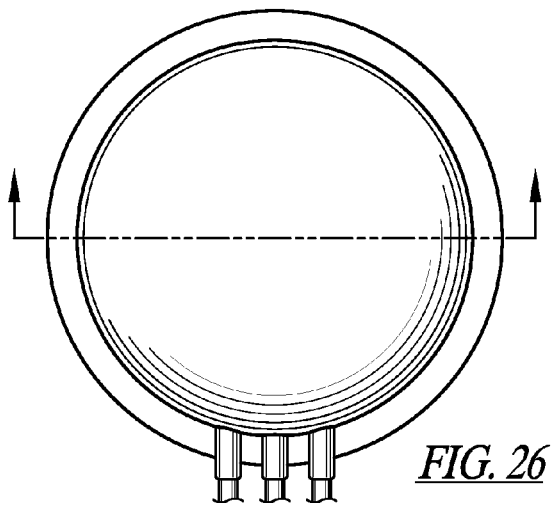
FIG. 26 depicts a substantially round multifunctional reservoir with three flexible tubing segments emanating from the reservoir.
Figure 26A:
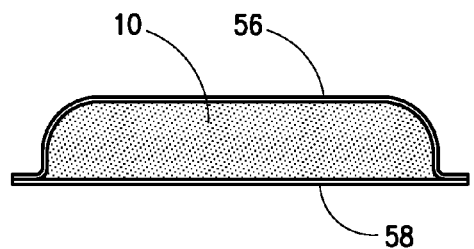
FIG. 26a is a cross-sectional view of the reservoir bladder depicted in FIG. 26 showing the configuration of a reservoir shell secured to a base, without the other components. The base extends peripherally beyond the reservoir shell.

FIG. 24, FIG. 25 and FIG. 26 depict fluid reservoir 10 shell or bladder construction without fluid transfer system and cylinder deflate mechanism components. FIG. 24A, FIG. 25A and FIG. 26A are cross-sectional views of FIG. 24, FIG. 25 and FIG. 26, respectively, and are intended to depict fabrication of the multifunctional reservoir fluid chamber.

FIG. 24A depicts reservoir bladder 56 with internal patch 57 that comprises fluid reservoir 10. Alternately, patch 57 could be secured to the exterior of reservoir bladder 56.

FIG. 25A depicts reservoir bladder 56 with base 58 extended beyond the periphery of reservoir bladder 56 that comprises fluid reservoir 10. The edge extension of base 56 provides a site for suture placement during surgical implantation.

FIG. 26A depicts reservoir bladder 56 with base 58 extended beyond the periphery of reservoir bladder 56 that comprises fluid reservoir 10. The edge extension of base 56 provides a site for suture placement during surgical implantation.

Reservoir bladder 56, patch 57 and base 58 may be fabricated from a thermoplastic elastomer such as polyurethane or thermoset elastomer such as silicone or other implantable grade elastomeric polymer. Base 58 preferably includes a woven reinforcement in the polymer matrix to provide dimensional stability and adequate tear strength for suturing the extended base during implantation. Depending on the materials selected, patch 57 and base 58 are secured to reservoir bladder 56 with solvent, adhesive or thermal bonds. With thermoset elastomers, patch 57 or base 58 may be attached by thermally processing an unvulanized layer of thermoset elastomer between previously vulcanized shell and patch or base.

Figure 27:
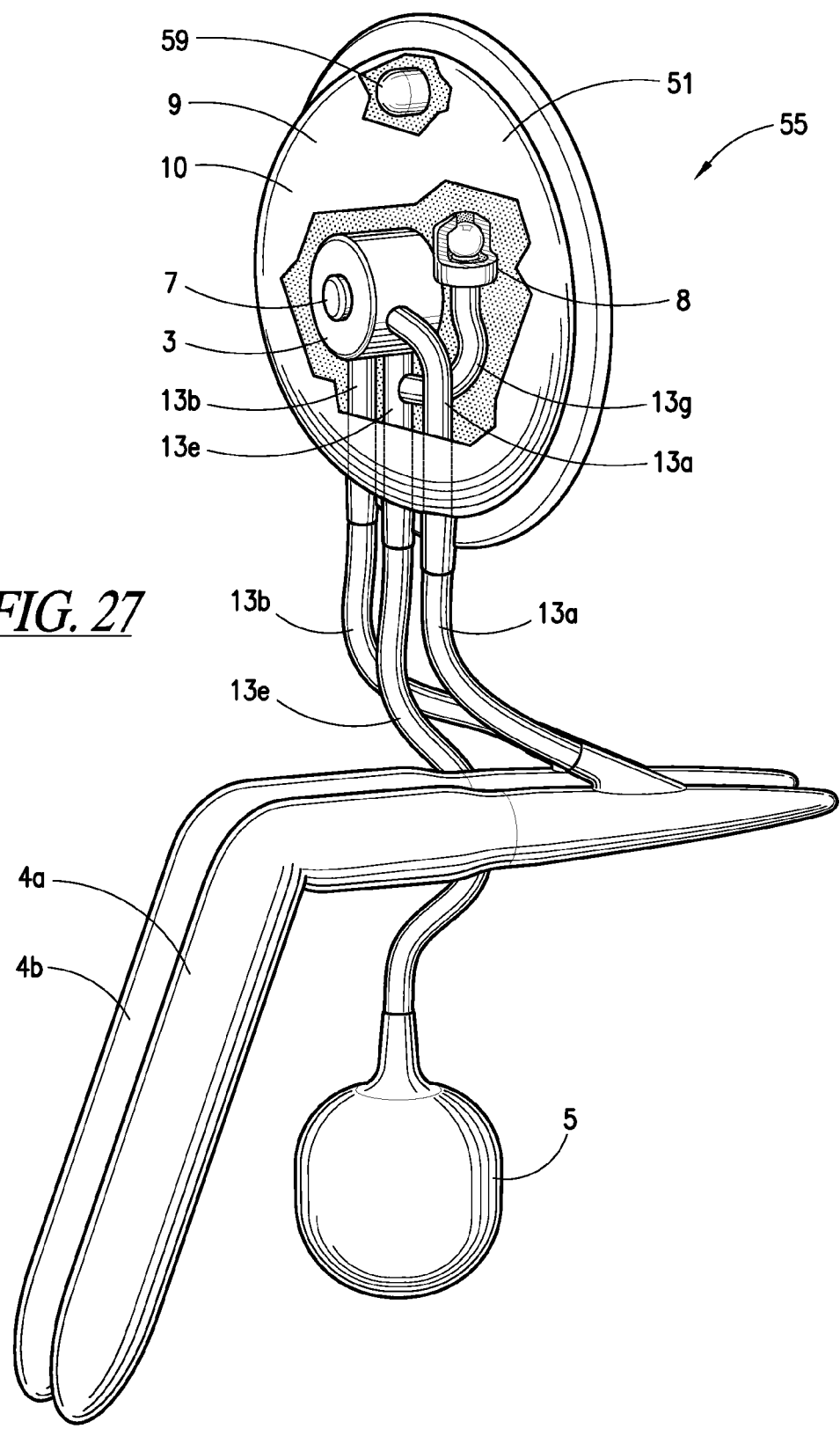
FIG. 27 depicts the inflatable penile prosthesis of FIG. 22 in the flaccid state with portions of the anterior wall of the reservoir removed to expose components within the reservoir.

FIG. 27 depicts inflatable penile prosthesis 55 as depicted in FIG. 22 with multifunctional reservoir 9 including fluid reservoir 10 with anterior wall 51 opened to expose inlet valve 8, spool valve assembly 3, deflate actuator button 7, fluid fill port 59 and flexible tubing 13a, 13b, 13e and 13g. Tubing 13e provides fluid communication between spool valve assembly 3 and fluid transfer bulb 5. Fluid transfer bulb 5 can be remotely located in the scrotum or abdomen. Flexible tubings 13a and 13b provide fluid communication between spool valve assembly 3 and inflatable penile cylinders 4a and 4b, respectively. Spool valve assembly 3 is depicted in and described in connection with FIG. 12 (deflate mode) and FIG. 13 (inflate mode).

Figure 28:
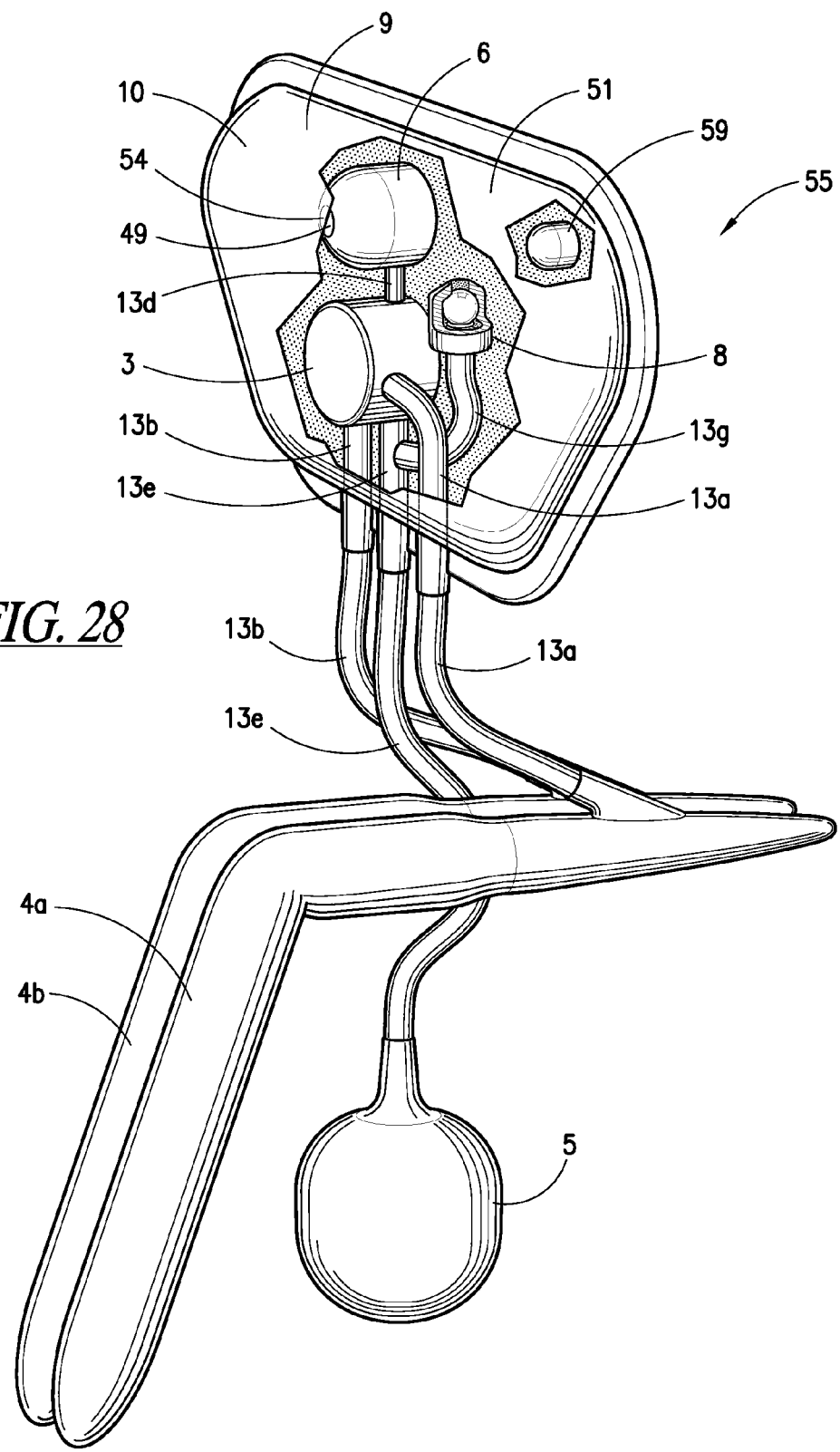
FIG. 28 depicts the inflatable penile prosthesis of FIG. 23 in the flaccid state with portions of the anterior wall of the reservoir removed to expose components within the reservoir.

FIG. 28 depicts inflatable penile prosthesis 55 as depicted in FIG. 23 with multifunctional reservoir 9 including fluid reservoir 10 with anterior wall 51 opened to expose inlet valve 8, spool valve assembly 3, deflate actuator bulb 6, fluid fill port 59 and flexible tubing 13a, 13b, 13d, 13e and 13g. Deflate actuator bulb 6 has aperture 49 through the apex of its dome that interacts with anterior wall 51 to comprise aperture valve 54. Flexible tubings 13a and 13b provide fluid communication between spool valve assembly 3 and inflatable penile cylinders 4a and 4b respectively. Spool valve assembly 3 is depicted in and described in connection with FIG. 9 (deflate mode) and FIG. 10 (inflate mode).

The Drawings illustrate a spool valve assembly that is designed for repeated assembly and disassembly for developmental purposes. Screws 25 used to retain end caps 22, 23 and 24 to housing 21 are convenient for developmental purposes, but would be an unlikely choice in the manufactured version. Instead, end caps 22, 23 and 24 might be secured to housing 21 by welding, bonding, snap fitting or press fitting. Valve seat retainer 41 could be eliminated in a manufactured version. O-rings 31, 32, 33 and 34 might be eliminated or replaced with wiper-type elements integrally molded onto the major diameter of a plastic spool or deflate actuator button. Deflate button pin 26 and deflate button screw 27, associated with deflate actuator button 7, are convenient for developmental efforts, but would likely be eliminated using alternative methods such as snap fit.

Materials for fabrication of the spool valve assembly components are preferably biocompatible rigid metals or plastics that will remain chemically and dimensionally stable when exposed to the hostile environment of human implantation. Biostable candidate metal materials for the housing, housing end caps, spool, spool end caps, balls, springs and spigots include a cobalt, nickel, chromium, molybdenum alloy known as MP35N or titanium alloy. Biostable candidate plastic materials for the housing, housing end caps, spool, valve poppets, spool end caps, spigots and deflate actuator button include polypropylene, polysulfone, polyetheretherketone (PEEK) and acrylic. Candidate elastomeric materials for the o-rings and valve seats include silicone and VITON® brand fluoroelastomer, commercially available from DuPont Performance Elastomers of Wilmington, Del.

Elastomeric o-rings or integrally molded wipers on a spool can be used to achieve a fluid seal between the spool and spool valve housing or create resistance to movement of the spool within the housing. Similarly, elastomeric o-rings or integrally molded wipers on the deflate actuator button can be used to achieve a fluid seal between the deflate actuator button and the spool valve housing or create resistance to movement of the deflate actuator button within the housing.

The present disclosure teaches providing an IPP comprising a fluid reservoir, at least one inflatable penile cylinder, a fluid transfer system to inflate the at least one penile cylinder with fluid from the fluid reservoir, a cylinder deflate mechanism to return fluid from the at least one inflatable penile cylinder to the fluid reservoir and a plurality of flexible tubing providing fluid communication between the components. The fluid transfer system comprises an inlet valve in fluid communication with the fluid reservoir; a fluid transfer bulb in fluid communication with the inlet valve; an exhaust valve in fluid communication with the fluid transfer bulb; and a spool valve assembly in fluid communication with the fluid transfer bulb and the at least one inflatable penile cylinder. The deflate mechanism comprises a spool valve assembly in fluid communication with the fluid reservoir and the at least one inflatable penile cylinder, a return valve in fluid communication with the reservoir and the at least one inflatable penile cylinder, and a deflate actuator to mechanically or hydraulically shift the spool valve assembly. The fluid transfer system is positioned to provide fluid communication between the fluid reservoir and the at least one inflatable penile cylinder. The deflate mechanism is positioned to provide fluid communication between the fluid reservoir and the at least one inflatable penile cylinder. The fluid transfer system and the deflate mechanism include a shared or common spool valve assembly.

The spool valve assembly acts as a two-position directional valve that is volitionally shifted to the cylinder inflate or cylinder deflate modes using forces external to the spool valve assembly. The spool valve assembly has a spool that can include an exhaust valve chamber to house an exhaust valve. The exhaust valve comprises an exhaust valve chamber, an exhaust valve spring, an exhaust valve ball or poppet and an exhaust valve seat. The spool valve assembly has a spool that can include a return valve chamber to house a return valve. The return valve comprises a return valve chamber, a return valve spring, a return valve ball or poppet and a return valve seat. The spool valve assembly is a two-position directional valve that can be shifted to the inflate mode with hydraulic pilot pressure from a fluid transfer bulb directed at the end of the spool that is ported to inflate at least the one inflatable penile cylinder. Alternately, the spool valve assembly can be shifted to the deflate mode with mechanical force from a deflate actuator button directed at the end of the spool that is ported to deflate the at least one inflatable penile cylinder. The spool valve assembly with the deflate actuator button that mechanically shifts the spool within the spool valve assembly to the deflate mode can have the deflate actuator button and the spool configured to provide fluid communication between a fluid reservoir and a headspace between the spool valve housing and the end of the spool ported to deflate the at least one inflatable cylinder. The headspace fluid communication with the fluid reservoir permits fluid to exit the headspace when the spool shifts to the inflate mode and enter the headspace when the spool shifts to the deflate mode, thus minimizing any resistance to spool movement.

The present disclosure teaches a two-piece IPP comprising a multifunctional fluid reservoir and at least one inflatable penile cylinder and flexible tubing connecting these components. The multifunctional fluid reservoir comprising a fluid transfer system to inflate the at least one penile cylinder with fluid from a fluid reservoir, a cylinder deflate mechanism to return fluid from the at least one inflatable penile cylinder to the fluid reservoir. The fluid transfer system comprises an inlet valve in fluid communication with the fluid reservoir, a fluid transfer bulb in fluid communication with the inlet valve, an exhaust valve in fluid communication with the fluid transfer bulb, a spool valve assembly in fluid communication with the fluid transfer bulb and the at least one inflatable penile cylinders and a plurality of flexible tubing providing fluid communication between the components of the fluid transfer system. The deflate mechanism comprises a spool valve assembly in fluid communication with the fluid reservoir and the at least one inflatable penile cylinder, a return valve in fluid communication with the reservoir and the at least one inflatable penile cylinder, and a deflate actuator to mechanically or hydraulically shift the spool valve assembly. The spool valve assembly acts as a two-position directional valve that is volitionally shifted to the cylinder inflate or cylinder deflate modes using external force applied to the spool within the spool valve assembly.

In one embodiment a multifunctional reservoir has a fluid reservoir segment with a substantially flat posterior wall or base and a curved anterior wall with a hollow space between the posterior wall and the anterior wall functioning as a fluid reservoir. One side of the base extends laterally beyond the fluid reservoir segment serving as a base for a fluid transfer bulb.

In another embodiment a multifunctional reservoir has a fluid reservoir segment with a substantially flat posterior wall or base and a curved anterior wall with a hollow space between the posterior and the anterior walls functioning as a fluid reservoir. The base extends laterally on both sides of the fluid reservoir segment serving as a base for a fluid transfer bulb on one side and a deflate actuator bulb on the opposite side. The deflate actuator bulb is surrounded by a lower profile extension of the anterior wall of the fluid reservoir, laterally extending the fluid reservoir to supply fluid to the deflate actuator bulb. The anterior wall surrounding the deflate actuator bulb cooperates with an aperture at the apex of the deflate actuator bulb covering the aperture to serve as an aperture valve. When the patient deforms the deflate actuator bulb the anterior wall contacts the aperture to close the aperture valve. The deflate bulb actuator is volitionally deformed causing fluid to be directed as pilot pressure to the end of a spool that is ported to deflate the at least one inflatable penile cylinder, thereby shifting the spool within the spool valve assembly actuating the deflate mechanism. The aperture valve opens in the absence of external force on the deflate actuator bulb so that the recovery of the deflate actuator bulb urges fluid to refill the deflate actuator bulb through the aperture valve. The aperture valve remains open to vent fluid from the spool valve assembly, allowing the spool to shift upon activation of the inflate mode.

A multifunctional fluid reservoir in either embodiment can have a fluid reservoir segment with an elongated shape. The elongated fluid reservoir segment can be between 1.5 and 3.0 inches wide and between 4.0 and 6.0 long. The multifunctional reservoir can have an overall width between 1.5 and 4.0 inches and an overall length between 5.0 and 11 inches. The fluid reservoir can have a fluid volume ranging from 50 to 150 cubic centimeters. It will be appreciated by those of ordinary skill in the art that these dimensions and volumes are provided for illustrative purposes only and are not intended to limit the scope of the present invention.

In another embodiment a multifunctional reservoir has a fluid reservoir segment with a substantially flat posterior wall or base and substantially flat anterior wall with a hollow space between the posterior and the anterior walls functioning as a fluid reservoir. A fluid transfer bulb is located remote from the multifunctional reservoir and is in fluid communication with the other components of the fluid transfer system with flexible tubing. The anterior wall surrounds the a deflate actuator bulb and cooperates with an aperture at the apex of the deflate actuator bulb, covering the aperture to serve as an aperture valve. When the patient deforms the deflate actuator bulb the anterior wall contacts the aperture to close the aperture valve. The deflate bulb actuator is volitionally deformed causing fluid to be directed as pilot pressure to the end of a spool that is ported to deflate the at least one inflatable penile cylinder, thereby shifting the spool within the spool valve assembly actuating the deflate mechanism. The aperture valve opens in the absence of external force on the deflate actuator bulb so that the recovery of the deflate actuator bulb urges fluid to refill the deflate actuator bulb through the aperture valve. The aperture valve remains open to vent fluid from the spool valve assembly, allowing the spool to shift upon activation of the inflate mode.

In the above embodiment, round, oval, triangular or multi-sided shapes with substantially parallel anterior and posterior surfaces may be adapted to achieve 50-150 cubic centimeter volume and anatomical conformity.

The present disclosure teaches a three-piece IPP comprising a fluid reservoir, at least one inflatable penile cylinder, a fluid transfer pump and flexible tubing connecting the components. The fluid transfer pump comprises a fluid transfer system having an inlet valve in fluid communication with the fluid reservoir, a fluid transfer bulb in fluid communication with the inlet valve, an exhaust valve in fluid communication with the fluid transfer bulb, a spool valve assembly in fluid communication with the fluid transfer bulb and the at least one inflatable penile cylinder, a deflate mechanism comprising a spool valve assembly in fluid communication with the fluid reservoir and the at least one inflatable penile cylinder, a return valve in fluid communication with the spool valve assembly and a deflate actuator to mechanically shift the spool valve assembly. The spool valve assembly acts as a two-position directional valve that is volitionally shifted to the cylinder inflate or cylinder deflate modes using forces external to the spool valve assembly. The spool valve assembly can be shifted to the inflate mode with hydraulic pilot pressure from the fluid transfer bulb directed at the end of the spool that is ported to inflate the at least one inflatable penile cylinder. The spool valve assembly can be shifted to the deflate mode with mechanical pressure from the deflate actuator button directed at the end of the spool that is ported to deflate the at least one inflatable penile cylinder.

Device Operation

The present disclosure teaches the incorporation of a two-position spool valve assembly into inflatable penile prostheses to either direct the flow of fluid into inflatable penile cylinders to provide a penile erection or to evacuate fluid out of the inflatable penile cylinders to cause the penis to be flaccid.

In the cylinder inflate mode, the fluid transfer bulb is deformed providing pilot pressure to shift the spool valve to the cylinder inflate mode, after which the exhaust valve within the spool opens releasing fluid into the inflatable penile cylinders. When the deformed fluid transfer bulb is released, it recovers to its original shape. Simultaneously with recovery of the fluid transfer bulb, the inlet valve opens to admit fluid from the reservoir to fill the bulb and the exhaust valve within the spool closes to prevent return of fluid from the cylinders to the fluid transfer bulb. The fluid transfer bulb is repeatedly deformed and released until the inflatable penile cylinders are substantially filled and have sufficient pressure to provide an erection of the penis.

The device is placed in the cylinder deflate mode by a volitional and instantaneous (as opposed to sustained) contact of the cylinder deflate actuator. The cylinder deflate actuator, either a mechanical or pilot pressure type, is used to shift the spool valve to the cylinder deflate position. In the deflate mode fluid flows from the inflated penile cylinders through the return valve and spool valve assembly to the fluid reservoir until the penis is flaccid. The spool valve assembly has a fluid pathway to route the fluid from the inflatable penile cylinders to the fluid reservoir during cylinder deflation. The spool also has a fluid pathway used to route the fluid from the cylinder port in the housing to the reservoir port in the housing during device deflation. A return valve located within the spool fluid pathway opens to allow fluid to return to the reservoir and closes to prevent fluid backflow to the inflatable penile cylinders.

Various modifications and additions can be made to the exemplary embodiments discussed without departing from the scope of the present invention. While the embodiments described above refer to particular features, the scope of this disclosure also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An inflatable penile prosthesis (IPP) comprising:
    a fluid reservoir;
    at least one inflatable penile cylinder;
    a fluid transfer system in fluid communication with the fluid reservoir and with the at least one inflatable penile cylinder to inflate the at least one penile cylinder with fluid from the fluid reservoir, the fluid transfer system comprising
        an inlet valve in fluid communication with the fluid reservoir,
        a fluid transfer bulb in fluid communication with the inlet valve,
        an exhaust valve in fluid communication with the fluid transfer bulb, and
        a spool valve assembly in fluid communication with the fluid transfer bulb and at least one inflatable penile cylinder; and
    a cylinder deflate mechanism in fluid communication with the fluid reservoir and with the at least one inflatable penile cylinder to return fluid from the at least one inflatable penile cylinder to the fluid reservoir, the cylinder deflate mechanism comprising
        the spool valve assembly,
        a return valve in fluid communication with the reservoir and the at least one inflatable penile cylinder, and
        a deflate actuator arranged to shift the spool valve assembly to a cylinder deflate mode,
    wherein the spool valve assembly can be shifted between a cylinder inflate mode and the cylinder deflate mode using a force external to the spool valve assembly.

2. The IPP of claim 1 wherein the spool valve assembly comprises a spool comprising an exhaust valve chamber to house the exhaust valve, the exhaust valve comprising:

an exhaust valve chamber;
an exhaust valve spring;
an exhaust valve ball or poppet; and
an exhaust valve seat.

3. The IPP of claim 1 wherein the spool valve assembly comprises a spool comprising a return valve chamber to house the return valve, the return valve comprising:
a return valve chamber;
a return valve spring;
a return valve ball or poppet; and
a return valve seat.

4. The IPP of claim 1 wherein the spool valve assembly is a two-position directional valve that can be shifted to the cylinder inflate mode with hydraulic pilot pressure from the fluid transfer bulb directed at the end of a spool that is ported to inflate the at least one inflatable penile cylinder.

5. The IPP of claim 1 wherein the spool valve assembly is a two-position directional valve that can be shifted to the cylinder deflate mode with hydraulic pilot pressure from a deflate actuator bulb directed at the end of a spool that is ported to deflate the at least one inflatable penile cylinder.

6. The IPP of claim 1 wherein the spool valve assembly is a two-position directional valve that can be shifted to the cylinder deflate mode with mechanical force from a deflate actuator button directed at the end of a spool that is ported to deflate the at least one inflatable penile cylinder.

7. The IPP of claim 6 wherein the deflate actuator button and the spool are configured to provide fluid communication between a fluid reservoir and a headspace between the spool valve housing and the end of the spool ported to deflate the at least one inflatable cylinder, thereby permitting fluid to exit the headspace when the spool shifts to the inflate mode and enter the headspace when the spool shifts to the cylinder deflate mode.

8. The IPP of claim 1 wherein the spool valve assembly is in fluid communication with the fluid transfer bulb.

9. A two-piece inflatable penile prosthesis (IPP) comprising:
at least one inflatable penile cylinder; and
a multifunctional fluid reservoir in fluid communication with the at least one inflatable penile cylinder, the multifunctional fluid reservoir comprising
a fluid transfer system to inflate the at least one penile cylinder, the fluid transfer system comprising
an inlet valve in fluid communication with a fluid reservoir,
a fluid transfer bulb in fluid communication with the inlet valve,
an exhaust valve in fluid communication with the fluid transfer bulb, and
a spool valve assembly in fluid communication with the fluid transfer bulb and the at least one inflatable penile cylinder, and
a cylinder deflate mechanism to return fluid from the at least one inflatable penile cylinder to the fluid reservoir, the cylinder deflate mechanism comprising
the spool valve assembly,
a return valve in fluid communication with the reservoir and the at least one inflatable penile cylinder, and
a deflate actuator to shift the spool valve assembly to a cylinder deflate mode,
wherein the spool valve assembly can be shifted between a cylinder inflate mode and the cylinder deflate mode using external force applied to a spool within the spool valve assembly.

10. The IPP of claim 9 wherein the spool valve assembly is a two-position directional valve that can be shifted to the cylinder inflate mode with hydraulic pilot pressure from the fluid transfer bulb directed at the end of the spool that is ported to inflate the at least one inflatable penile cylinder.

11. The IPP of claim 9 wherein the spool valve assembly is a two-position directional valve that can be shifted to the cylinder deflate mode with hydraulic pilot pressure from the deflate actuator bulb directed at the end of the spool that is ported to deflate at least one inflatable penile cylinder.

12. The IPP of claim 9 wherein the spool valve assembly is a two-position directional valve that can be shifted to the cylinder deflate mode with mechanical pressure from the deflate actuator button directed at the end of the spool that is ported to deflate at least one inflatable penile cylinder.

13. The IPP of claim 12 wherein the deflate actuator button and the spool valve assembly are configured to provide fluid communication between the fluid reservoir and a headspace between the spool valve housing and the end of the spool ported to deflate the at least one inflatable cylinder, permitting fluid to exit the headspace when the spool shifts to the inflate mode and enter the headspace when the spool shifts to the cylinder deflate mode.

14. The IPP of claim 9, wherein the multifunctional reservoir has a fluid reservoir segment with a substantially flat posterior wall and a curved anterior wall, wherein a hollow space between the posterior wall and the anterior wall functions as the fluid reservoir; and wherein one side of the posterior wall extends laterally beyond said fluid reservoir segment and serves as a base for said fluid transfer bulb.

15. The IPP of claim 9, wherein the multifunctional reservoir has a fluid reservoir segment with a substantially flat posterior wall and a curved anterior wall, wherein a hollow space between the posterior wall and the anterior wall functions as said fluid reservoir, the posterior wall extends laterally on both sides of the fluid reservoir segment serving as a base for said fluid transfer bulb on one side and a deflate actuator bulb on the opposite side, wherein the deflate actuator bulb is surrounded by a lower profile extension of the anterior wall of the fluid reservoir, laterally extending the fluid reservoir to supply fluid to the deflate actuator bulb.

16. The IPP of claim 9, wherein the multifunctional reservoir comprises a fluid reservoir segment having a posterior wall and an anterior wall that define a hollow space that serves as a fluid reservoir, wherein the deflate actuator comprises a deflate actuator bulb located within the hollow space, the deflate actuator bulb having a dome with an apex and an aperture located at the apex, and wherein the anterior wall substantially surrounds the deflate actuator bulb and covers the aperture to serve as an aperture valve.

17. A three-piece inflatable penile prosthesis (IPP) comprising:
a fluid reservoir;
at least one inflatable penile cylinder in fluid communication with the fluid reservoir; and
a fluid transfer pump in fluid communication with the fluid reservoir and with the at least one inflatable penile cylinder, the fluid transfer pump comprising
a fluid transfer system comprising
an inlet valve in fluid communication with the fluid reservoir,
a fluid transfer bulb in fluid communication with the inlet valve,
an exhaust valve in fluid communication with the fluid transfer bulb, and a spool valve assembly in fluid communication with the fluid transfer bulb and the at least one inflatable penile cylinder; and
a deflate mechanism comprising
a spool valve assembly in fluid communication with the fluid reservoir and the at least one inflatable penile cylinder,
a return valve in fluid communication with the reservoir and the at least one inflatable penile cylinder, and
a deflate actuator button to mechanically shift the spool valve to a cylinder deflate mode;
wherein the spool valve assembly can be shifted between a cylinder inflate mode and the cylinder deflate mode using a force external to the spool valve assembly.

18. The IPP of claim 17 wherein the spool valve assembly is configured with its central axis aligned perpendicular to the central axis of the fluid transfer bulb.

19. The IPP of claim 17 wherein the spool valve assembly is configured with its central axis corresponding to the central axis of the fluid transfer bulb.

20. An inflatable penile prosthesis (IPP) comprising:
a fluid reservoir;
at least one inflatable penile cylinder;
a fluid transfer system to inflate the at least one penile cylinder with fluid from the fluid reservoir; and
a deflate mechanism to return fluid from the at least one inflatable penile cylinder to the fluid reservoir,
wherein the fluid reservoir, the at least one inflatable penile cylinder, the fluid transfer system, and the deflate mechanism are all in fluid communication with one another,
wherein the fluid transfer system is positioned to provide fluid communication between the fluid reservoir and the at least one inflatable penile cylinder,
wherein the deflate mechanism is positioned to provide fluid communication between the fluid reservoir and the at least one inflatable penile cylinder, and
wherein the fluid transfer system and the deflate mechanism include a shared spool valve assembly.

21. The IPP of claim 20 wherein the spool valve assembly is a two-position directional valve that can be shifted to the cylinder inflate mode with hydraulic pilot pressure from the fluid transfer bulb directed at the end of the spool that is ported to inflate the at least one inflatable penile cylinder.

22. The IPP of claim 20 wherein the spool valve assembly is a two-position directional valve that can be shifted to the cylinder deflate mode with mechanical pressure from the deflate actuator button directed at the end of the spool that is ported to deflate the at least one inflatable penile cylinder.

23. An inflatable penile prosthesis (IPP) comprising:
a fluid reservoir;
at least one inflatable penile cylinder; and
a fluid transfer system including a fluid transfer pump, a deflate mechanism and a shared spool valve assembly, the shared spool valve assembly comprising
a housing with cylindrical bore and fluid ports associated with the fluid transfer system and the deflate mechanism,
a spool capable of shifting axially within the housing to cooperate with the fluid ports in the housing, the spool including
a fluid transfer system channel,
an exhaust valve located within the fluid transfer channel in the spool to prevent backflow from the at least one inflatable penile cylinder to the fluid transfer pump,
a deflate mechanism fluid channel, and
a return valve located within the deflate mechanism fluid channel in the spool to prevent backflow from the fluid reservoir to the at least one inflatable penile cylinder,
wherein the spool valve can be shifted between a cylinder inflate mode and a cylinder deflate mode using a force external to the spool valve.

24. An inflatable penile prosthesis (IPP) comprising:
a fluid reservoir having a substantially flat posterior base comprising a reinforced elastomeric base to maintain dimensional stability;
at least one inflatable penile cylinder;
a fluid transfer system to inflate the at least one inflatable penile cylinder with fluid from the fluid reservoir; and
a deflate mechanism to return fluid from the at least one inflatable penile cylinder to the fluid reservoir.

25. The IPP of claim 24, wherein the fluid reservoir comprises a fluid bladder, and wherein the base extends peripherally beyond the fluid bladder and forms a site for suture placement during surgical implantation.

* * * * *